United States Patent
Ágoston et al.

(10) Patent No.: US 8,889,637 B2
(45) Date of Patent: Nov. 18, 2014

(54) POLYMORPHS OF 2'-O-FUCOSYLLACTOSE AND PRODUCING THEREOF

(75) Inventors: Károly Ágoston, Telki (HU); István Bajza, Debrecen (HU); Gyula Dekany, Sinnamon Park (AU); Péter Trinka, Budapest (HU); Ágnes Ágoston, Telki (HU); Gábor Kádár, Budapest (HU); Sándor Demkó, Debrecen (HU); Ignacio Figueroa-Pérez, Miami, FL (US); Markus Hederos, Svedala (SE); Ferenc Horváth, Pilisszentkereszt (HU); Andreas Schroven, Barssel (DE); Ioannis Vrasidas, Salonika (GR); Piroska Kovács-Pénzes, Jászberény (HU); Christian Risinger, Rottweil (DE); László Kalmár, Váncsod (HU); Gergely Pipa, Budapest (HU); Julien Boutet, La Plaine sur Mer (FR); Lars Kröger, Hamburg (DE); Christoph Röhrig, Mühlingen (DE)

(73) Assignee: Glycom A/S, Kongens Lyngby (DK)

( * ) Notice: Subject to any disclaimer, the term of this patent is extended or adjusted under 35 U.S.C. 154(b) by 77 days.

(21) Appl. No.: 13/701,085

(22) PCT Filed: Jun. 1, 2011

(86) PCT No.: PCT/DK2011/050192
§ 371 (c)(1),
(2), (4) Date: Mar. 14, 2013

(87) PCT Pub. No.: WO2011/150939
PCT Pub. Date: Dec. 8, 2011

(65) Prior Publication Data
US 2013/0165406 A1 Jun. 27, 2013

(30) Foreign Application Priority Data
Jun. 1, 2010 (DK) .................................. 2010 70233

(51) Int. Cl.
*A61K 31/70* (2006.01)
*C07H 1/00* (2006.01)
*C07H 3/06* (2006.01)
*A23L 1/09* (2006.01)
*A23L 1/30* (2006.01)
*C07H 1/06* (2006.01)

(52) U.S. Cl.
CPC ... *C07H 3/06* (2013.01); *A23L 1/09* (2013.01); *A23L 1/30* (2013.01); *C07H 1/06* (2013.01)

USPC .............................. 514/23; 536/1.11; 536/123

(58) Field of Classification Search
CPC ......................................................... C07H 3/06
USPC ........................................................... 536/123
See application file for complete search history.

(56) References Cited

FOREIGN PATENT DOCUMENTS

| WO | WO9843494 | 10/1998 |
|---|---|---|
| WO | 2010/070616 | 6/2010 |
| WO | 2010/115934 | 10/2010 |
| WO | 2010/115935 | 10/2010 |

OTHER PUBLICATIONS

International Search Report mailed Jul. 4, 2011, in connection with International Application No. PCT/DK2011/050192, filed Jun. 1, 2011.
Kuhn R et al, "Kristalliserte Fucosido-lactose" Chem Ber 1956, vol. 89(11) p. 2513 (translation).
Kuhn R et al, "Fucosido-lactose, das Trisaccharid der Frauen milch," Chem Ber 1955, vol. 88(8) pp. 1135-1146 (translation).
Abbas, S.A., et al., "Synthesis of O-a-L-Fucopyranosyl-(1,2)-O-b-D-Galactopyranosyl-(1-4)-D-Glucopyranose (2'-O-a-L-Fucopyranosyl-lactose)" Carbohydr Res 1981, vol. 88(1) pp. 51-60.
Fernandez-Mayorales, A., et al., "Synthesis of 3- and 2'-fucosyl-lactose and 3,2'-difucosyl-lactose from partially benzylated lactose derivatives" Carbohydr Res 1986, vol. 154(1) pp. 93-101.
Izumi, M. et al, "Syntheisi of 5-Thio-L-fucose-Containing Disaccharides, as Sequence-Specific Inhibitors, and 2'-Fucosyllactose, as a Substrate of α-L-Fucosidases", Journal of Organic Chemistry, vol. 62, pp. 992-998, (1997).

*Primary Examiner* — Elli Peselev
(74) *Attorney, Agent, or Firm* — McHale & Slavin, P.A.

(57) ABSTRACT

The present invention relates to novel polymorphs of the trisaccharide 2'-O-fucosyllactose (2-FL) of formula (1), methods for producing said polymorphs and their use in pharmaceutical or nutritional compositions.

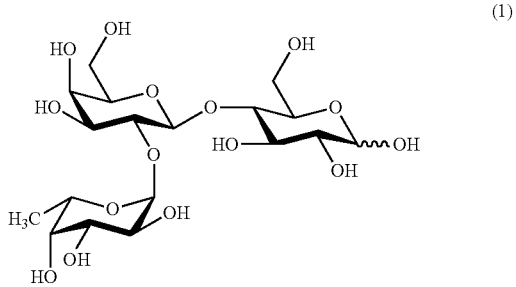

(1)

20 Claims, 19 Drawing Sheets

POLYMORPHS OF 2'-O-FUCOSYLLACTOSE AND PRODUCING THEREOF

CROSS-REFERENCE TO RELATED APPLICATIONS

This application is a §371 national stage entry of International Application No. PCT/DK2011/050192, filed Jun. 1, 2011, which claims priority to Danish Patent Application No. PA 2010-70233 filed Jun. 1, 2010, the entire contents of which are incorporated herein by reference.

FIELD OF THE INVENTION

The present invention provides novel polymorphs of the trisaccharide 2-FL, producing thereof and formulations containing the same.

BACKGROUND OF THE INVENTION

In the present years commercialization efforts for the synthesis of complex carbohydrates including secreted oligosaccharides have increased significantly due to their roles in numerous biological processes occurring in living organisms. Secreted oligosaccharides such as human milk oligosaccharides are becoming important commercial targets for nutrition and therapeutic industries. However, the syntheses and purification of these oligosaccharides and their intermediates remained a challenging task for science. One of the most important human milk oligosaccharides is 2'-O-fucosyllactose (2-FL, see Scheme 1) found in the highest concentration in mother's milk.

Scheme 1

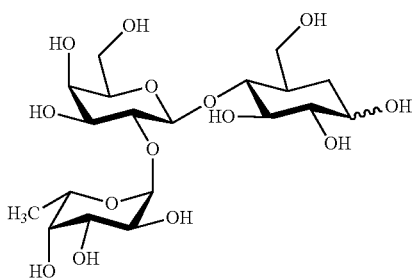

Several biological roles of 2'-O-fucosyllactose have been suggested including but not limited to its prebiotic, antibacterial, antiviral, immune system enhancing, brain development enhancing, etc. effects making it an attractive target for large scale production/isolation/purification for nutritional and therapeutic industries.

The first mention of 2'-O-fucosyllactose in the literature appeared in the 1950's by Kuhn et al. (*Chem. Ber.* 1955, 88, 1135; ibid. 1956, 89, 2513). According to the method by Kuhn syrupy or amorphous 2-FL isolated from mother's milk was dissolved in hot 75% methanol and abs. ethanol was gradually added in the presence of seed crystals. The seed crystals were produced in two ways: after "prolonged" storage some small crystals precipitated by the wall of the flask containing syrupy 2-FL, or 2-FL precipitated from a solution consisting of aqueous methanol, n-butanol and n-hexanol at 4° C. after "several" weeks. The crystalline 2-FL thus obtained had the melting point of 230-231° C. (decomposed), contained no constitutional water and was supposed to be the α-form.

At those times specific human milk oligosaccharides were isolated from human milk by using sophisticated chromatographic protocols (mainly paper chromatography). However, the purities of such early isolated samples are rather uncertain due to the high number of human milk oligosaccharide isomers present in mother's milk and due to lack of availability of high performance chromatography techniques which are nowadays usual in the investigation and resolution of such complex tasks. For example, 2'-O-fucosyllactose and 3-O-fucosyllactose are both present in human milk and their chromatographic separation have been solved decades later. Though 2-FL was reported as a crystalline compound by Kuhn in 1956, because of the considerations mentioned above the purity of the isolated sample is rather ambiguous. Furthermore, since that publication no other evidence, reference or indication on the crystalline existence or occurrence of 2-FL could have been found in the art, thus 2-FL is generally available and used as amorphous (lyophilized) solid.

Crystallization or recrystallization is one of the simplest and cheapest methods to separate a product from contaminations and obtain pure substance. In addition, providing one or more crystalline modifications (polymorphs) of a solid is an important factor in product development, because the different crystalline forms affect the compound's properties—for example thermodynamic stability, solubility, density, hygroscopicity, electrical properties (such as dielectric constant, conductivity), mechanical properties (such as friability, hardness, breaking strength, elasticity), optical properties (such as colour, transparency, refraction), etc. —diversely. It enlarges the repertoire of materials that a scientist has available for improving the product's characteristics. With respect of 2-FL there is still a need for crystalline product which may simplify isolation, purification and formulation problems so far envisaged.

SUMMARY OF THE INVENTION

The present invention provides crystalline 2'-O-fucosyllactose polymorphs and methodologies suitable for large scale purification of 2'-O-fucosyllactose. Thus, the crystalline products provided by the present invention are responsible for the development of high purity 2'-O-fucosyllactose for nutritional and pharmaceutical industries.

BRIEF DESCRIPTION OF THE FIGURES

The invention will be described in further detail hereinafter with reference to the accompanying figures, in which.

DETAILED DISCLOSURE OF THE INVENTION

The present inventors have found that 2'-O-fucosyllactose can be obtained in different crystalline forms.

Crystalline 2'-O-fucosyllactose polymorph I, either as polycrystalline material or as single crystal, comprises X-ray powder diffraction reflections, based on a measurement using CuKα radiation, at 21.34±0.20, 20.92±0.20 and 18.37±0.20 2Θ angles, more preferably at 21.34±0.20, 20.92±0.20, 18.37±0.20 and 16.70±0.20 2Θ angles, even more preferably at 21.34±0.20, 20.92±0.20, 18.37±0.20, 16.70±0.20 and 9.91±0.20 2Θ angles, most preferably at 21.34±0.20, 20.92±0.20, 18.37±0.20, 16.70±0.20, 9.91±0.20 and 13.13±0.20 2Θ angles, in particular at 21.34±0.20, 20.92±0.20, 18.37±0.20, 16.70±0.20, 9.91±0.20, 13.13±0.20, 7.87±0.20 and 8.90±0.20 2Θ angles. List of peaks of the XRPD pattern of crystalline 2'-O-fucosyllactose polymorph I is reported in Table 1.

TABLE 1

List of peaks of the XRPD pattern of crystalline 2'-O-fucosyllactose polymorph I

| 2Θ | rel. |
|---|---|
| 7.87 | 23 |
| 8.90 | 22 |
| 9.91 | 31 |
| 12.46 | 13 |
| 13.13 | 23 |
| 13.61 | 13 |
| 13.84 | 5 |
| 15.80 | 3 |
| 16.70 | 31 |
| 17.19 | 13 |
| 18.37 | 38 |

TABLE 1-continued

List of peaks of the XRPD pattern of crystalline 2'-O-fucosyllactose polymorph I

| 2Θ | rel. |
|---|---|
| 18.54 | 16 |
| 19.34 | 6 |
| 19.76 | 7 |
| 20.40 | 6 |
| 20.92 | 46 |
| 21.34 | 100 |
| 21.79 | 11 |
| 22.22 | 3 |
| 22.68 | 4 |
| 23.75 | 3 |
| 25.10 | 16 |
| 26.01 | 14 |
| 26.48 | 4 |
| 26.83 | 7 |
| 27.98 | 8 |
| 28.58 | 6 |
| 29.24 | 3 |
| 30.20 | 2 |
| 30.57 | 3 |
| 31.58 | 4 |
| 31.74 | 4 |
| 33.49 | 6 |
| 33.88 | 2 |
| 34.30 | 3 |
| 35.68 | 9 |
| 36.12 | 8 |
| 36.31 | 9 |
| 36.75 | 4 |
| 37.36 | 3 |
| 37.64 | 3 |
| 38.28 | 2 |
| 39.73 | 4 |
| 40.22 | 5 |
| 40.43 | 5 |
| 40.93 | 4 |
| 41.76 | 2 |
| 42.54 | 3 |
| 43.64 | 2 |

The XRPD patterns of different samples of crystalline 2'-O-fucosyllactose polymorph I are shown in FIGS. 1-4.

Crystalline 2'-O-fucosyllactose polymorph I has a characteristic IR peak at 3428±4 cm$^{-1}$, preferably has characteristic IR peaks at 3428±4 and 1021±4 cm$^{-1}$, more preferably at 3428±4, 1021±4 and 1039±4 cm$^{-1}$, even more preferably at 3428±4, 1021±4, 1039±4 and 1066±4 cm$^{-1}$, in particular at 3428±4, 1021±4, 1039±4, 1066±4, 1088±4, 1113±4, 1133±4, 1165±4, 1346±4, 1389±4, 1451±4, 2916±4, 2956±4 and 2975±4 cm$^{-1}$.

Figure 7:
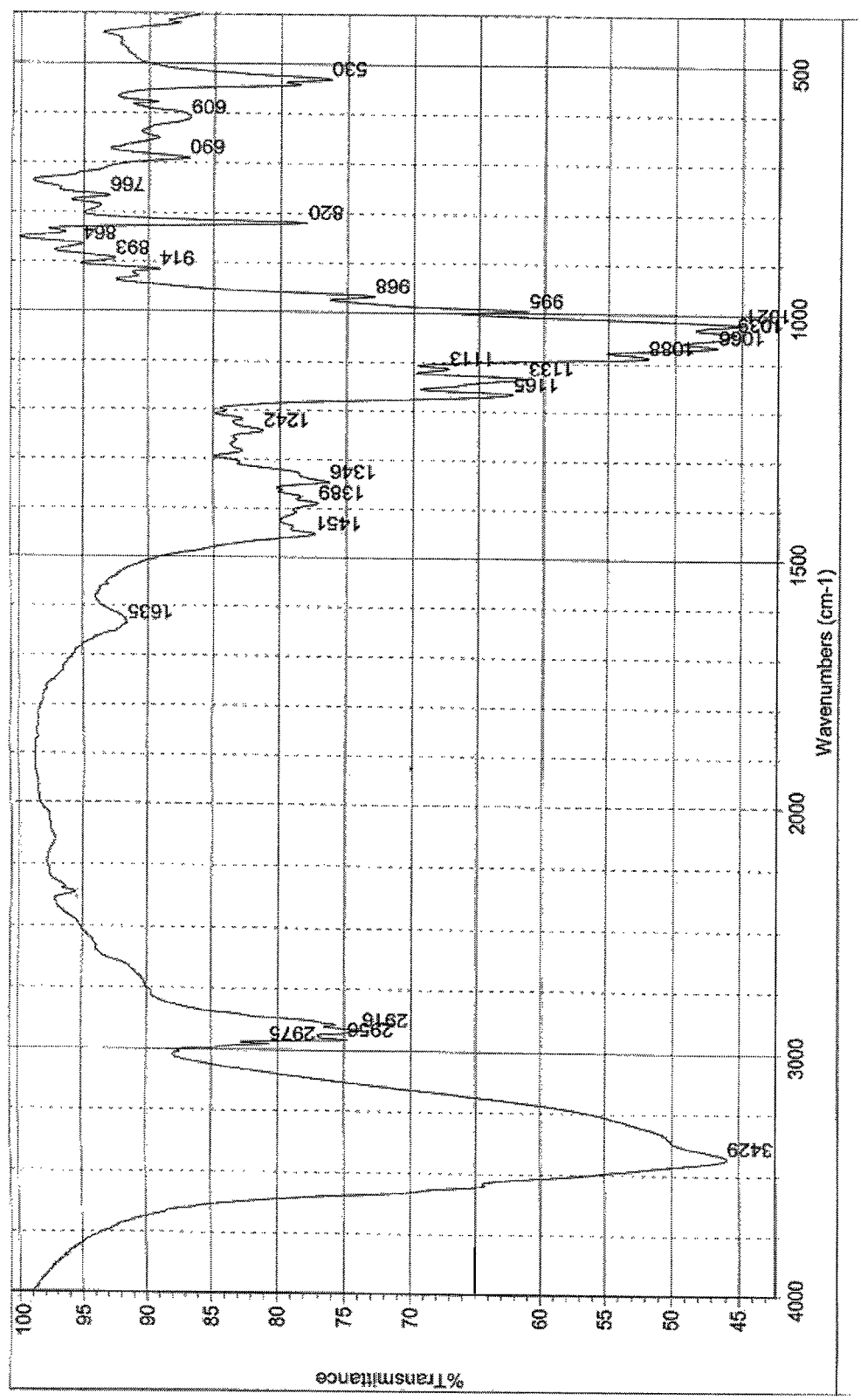
FIG. 7 shows the IR spectrum of crystalline 2'-O-fucosyllactose polymorph I.

The IR spectrum of crystalline 2'-O-fucosyllactose polymorph I is shown in FIG. 7.

Figure 6:
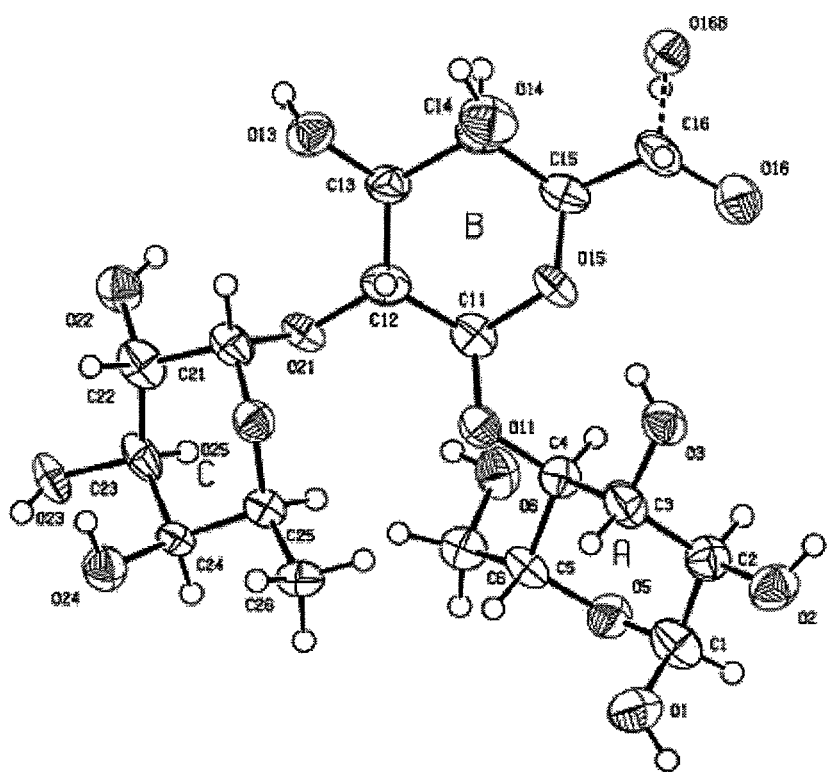
FIG. 6 shows the single crystal structure of 2'-O-fucosyllactose polymorph I.

The novel crystalline polymorph I of 2-FL can be considered as an anomeric mixture of α- and β-anomers or even pure form of one of the anomers. If 2-FL polymorph I is isolated as a polycrystalline material, it forms a mixture of α- and β-anomers, wherein the α-anomer is predominant over the β-anomer and at most 30% of β-anomer, preferably 7-25% of β-anomer is present according to solid-state $^{13}$C-NMR measurements. If 2'-O-fucosyllactose polymorph I is obtained as single crystal, it exists in the monoclinic system, space group P2$_1$, and has the following crystal cell parameters: a=10.1781 (11) Å, b=9.1990(9) Å, c=11.7332(13) Å, α=90.00°, β=107.871(3)°, γ=90.00°. No constitutional water and/or solvent are incorporated in the crystal structure. The anomeric OH-group occupies axial position that is it concerns O-(α-L-fucopyranosyl)-(1→2)-O-(β-D-galactopyranosyl)-(1→4)-α-D-glucose (see FIG. 6). The details of crystal data and structure refinement for crystalline 2'-O-fucosyllactose polymorph I are given in Table 2.

TABLE 2

Single crystal parameters for crystalline 2'-O-fucosyllactose polymorph I

| DATA | crystalline 2'-O-fucosyllactose polymorph I |
|---|---|
| Empirical formula | $C_{18}H_{31}O_{15}$ |
| Formula weight | 487.43 |
| Temperature | 93(2) K |
| Radiation and wavelength | Mo—$K_\alpha$, $\lambda = 0.71075$ Å |
| Crystal system | monoclinic |
| Space group | P $2_1$ |
| Unit cell dimensions | a = 10.1781(11) Å |
| | b = 9.1990(9) Å |
| | c = 11.7332(13) Å |
| | $\alpha = 90.00°$ |
| | $\beta = 107.871(3)°$ |
| | $\gamma = 90.00°$ |
| Volume | 1045.55(19) Å$^3$ |
| Z | 2 |
| Density (calculated) | 1.548 g/cm$^3$ |
| Absorption coefficient, $\mu$ | 0.137 mm$^{-1}$ |
| F(000) | 518 |
| Crystal colour | colourless |
| Crystal description | prism |
| Crystal size | 0.13 × 0.05 × 0.05 mm |
| Absorption correction | numerical |
| Max. and min. transmission | 0.990 and 0.977 |
| Θ-range for data collection | $3.05 \leq \theta \leq 21.49°$ |
| Index ranges | $-10 \leq h \leq 10$; $-9 \leq k \leq 9$; $-12 \leq l \leq 12$ |
| Reflections collected | 8050 |
| Completeness to 2θ | 0.997 |
| Independent reflections | 2399 [R(int) = 0.1322] |
| Reflections I > 2σ(I) | 1424 |
| Refinement method | full-matrix least-squares on F2 |
| Data/restraints/parameters | 2399/19/312 |
| Goodness-of-fit on F2 | 0.918 |
| Extinction coefficient | 0.018(3) |
| Final R indices [I > 2σ(I)] | R1 = 0.0604, wR2 = 0.1124 |
| R indices (all data) | R1 = 0.1093, wR2 = 0.1319 |
| Max. and mean shift/esd | 0.544; 0.005 |
| Largest diff. peak and hole | 0.26 and −0.29 e · Å$^{-3}$ |

The tests and procedures used to obtain the data included in Table 2 are standard in the art and a person skilled in the art would know how to carry out these tests based on this specification and his/her knowledge of the art.

Figure 1:
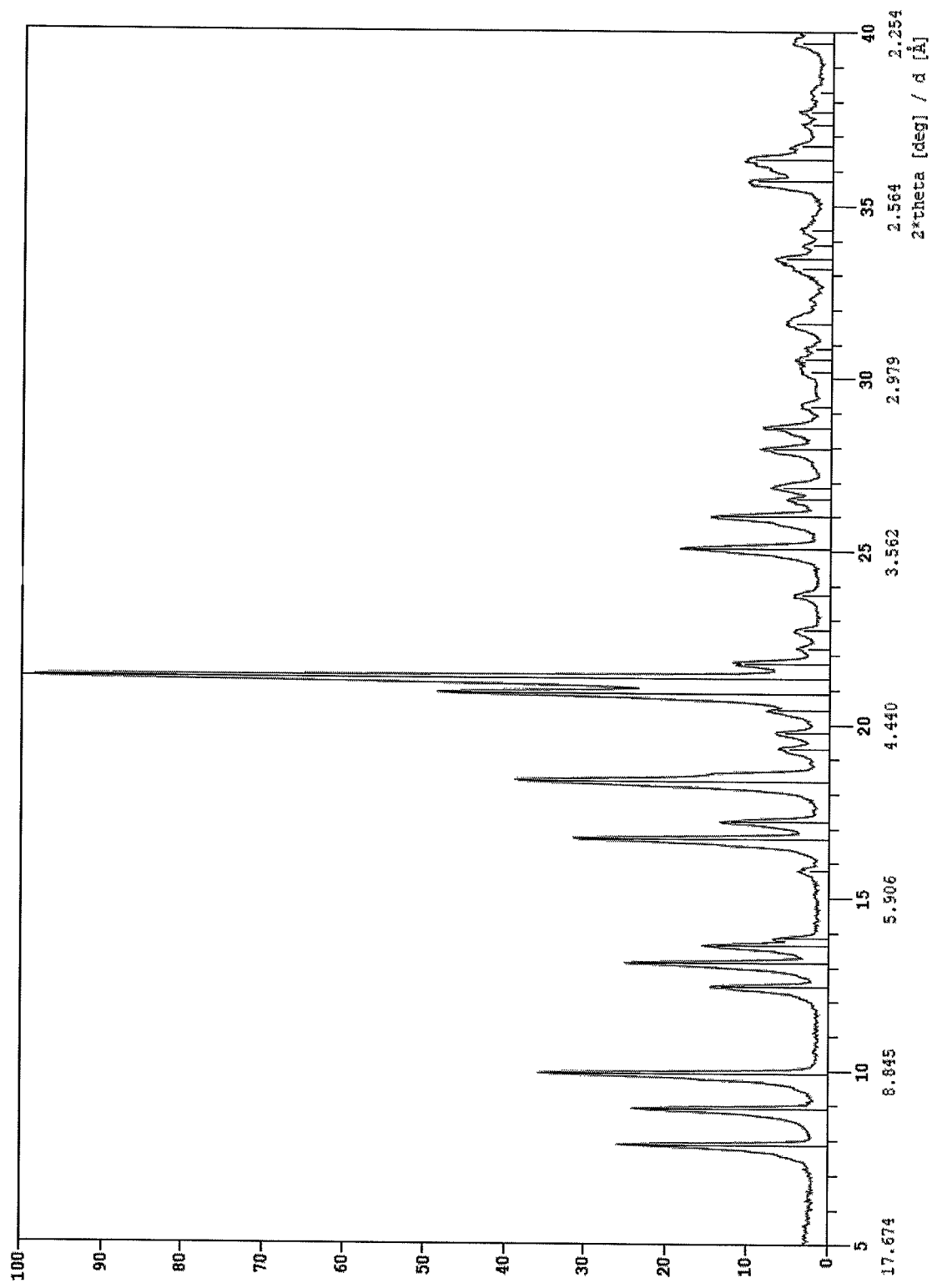
FIG. 1 shows the X-ray powder diffraction pattern of crystalline 2'-O-fucosyllactose polymorph I according to example A, item 1.
Figure 2:
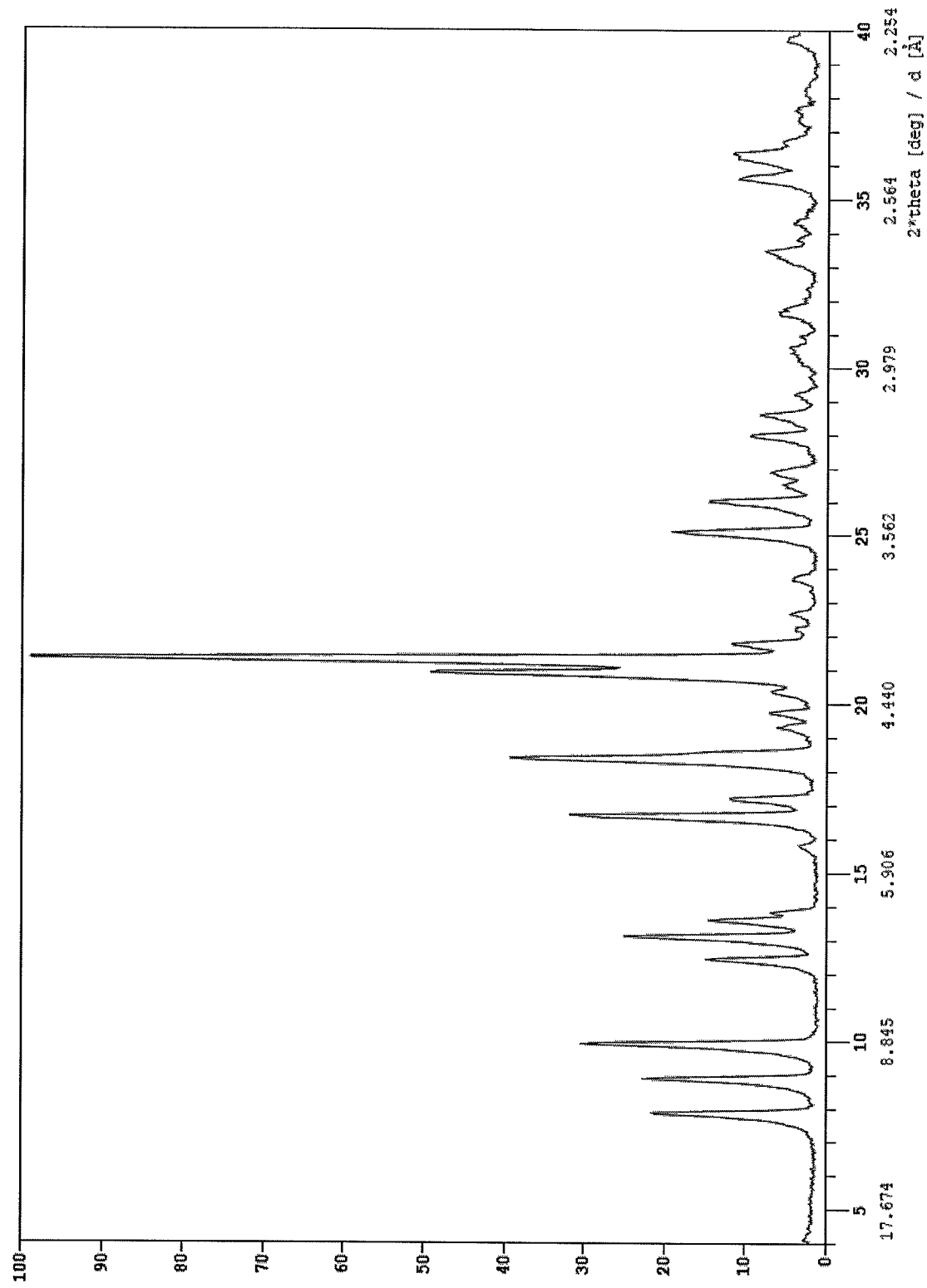
FIG. 2 shows the X-ray powder diffraction pattern of crystalline 2'-O-fucosyllactose polymorph I according to example C.
Figure 3:
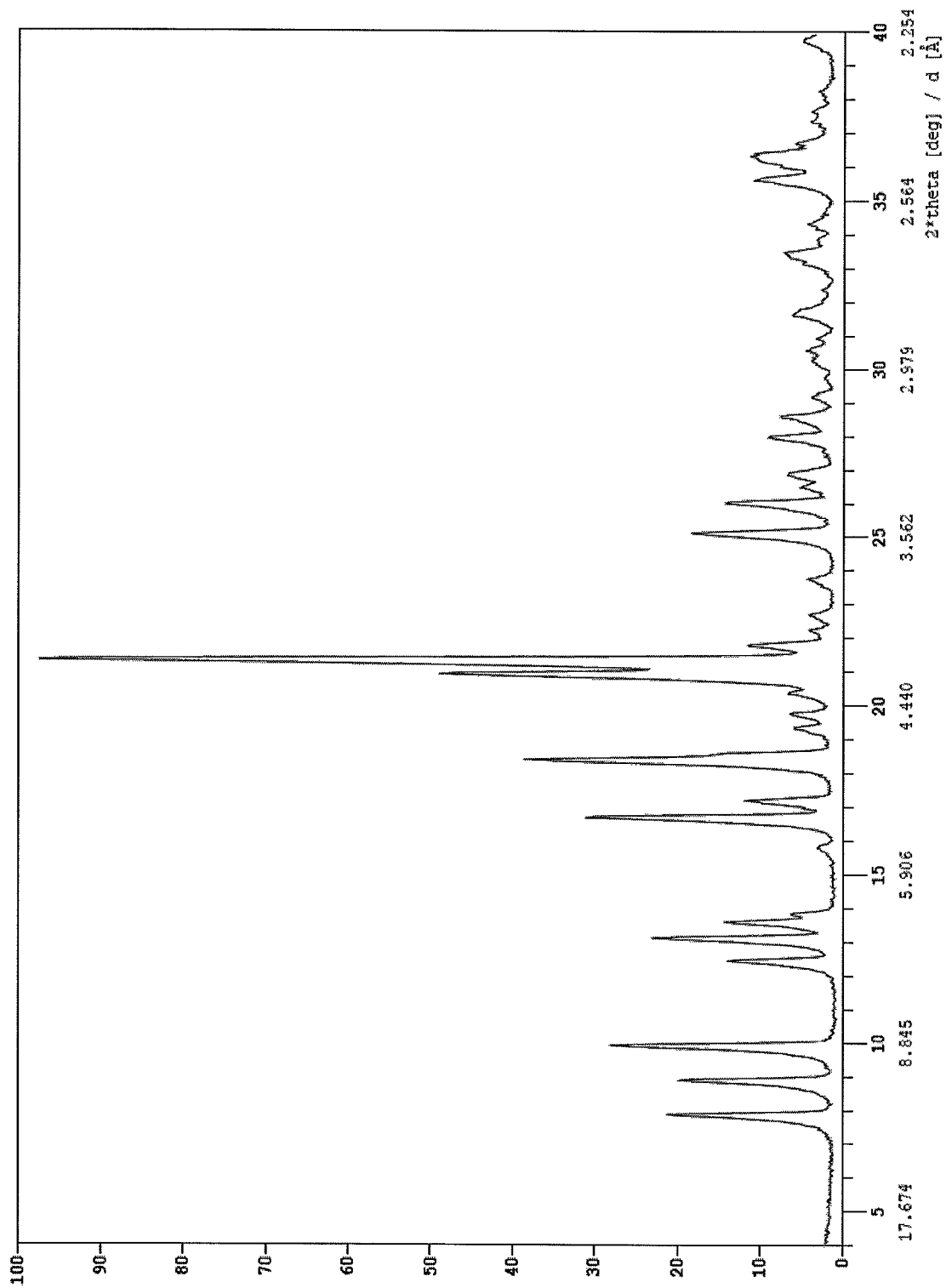
FIG. 3 shows the X-ray powder diffraction pattern of crystalline 2'-O-fucosyllactose polymorph I according to example D.
Figure 4:
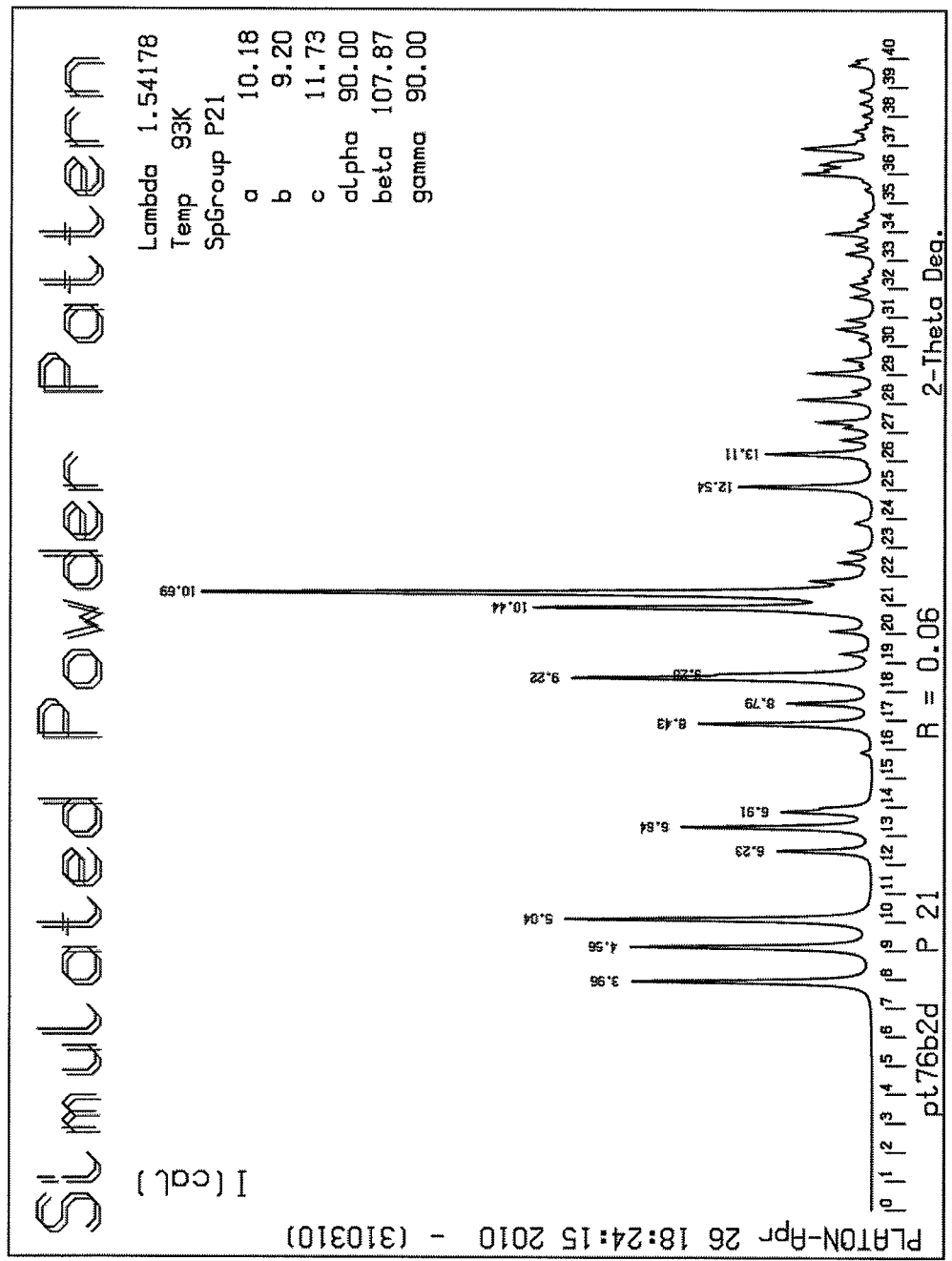
FIG. 4 shows the calculated X-ray powder diffraction pattern from the single crystal structure of 2'-O-fucosyllactose polymorph I for CuKα radiation.
Figure 5:
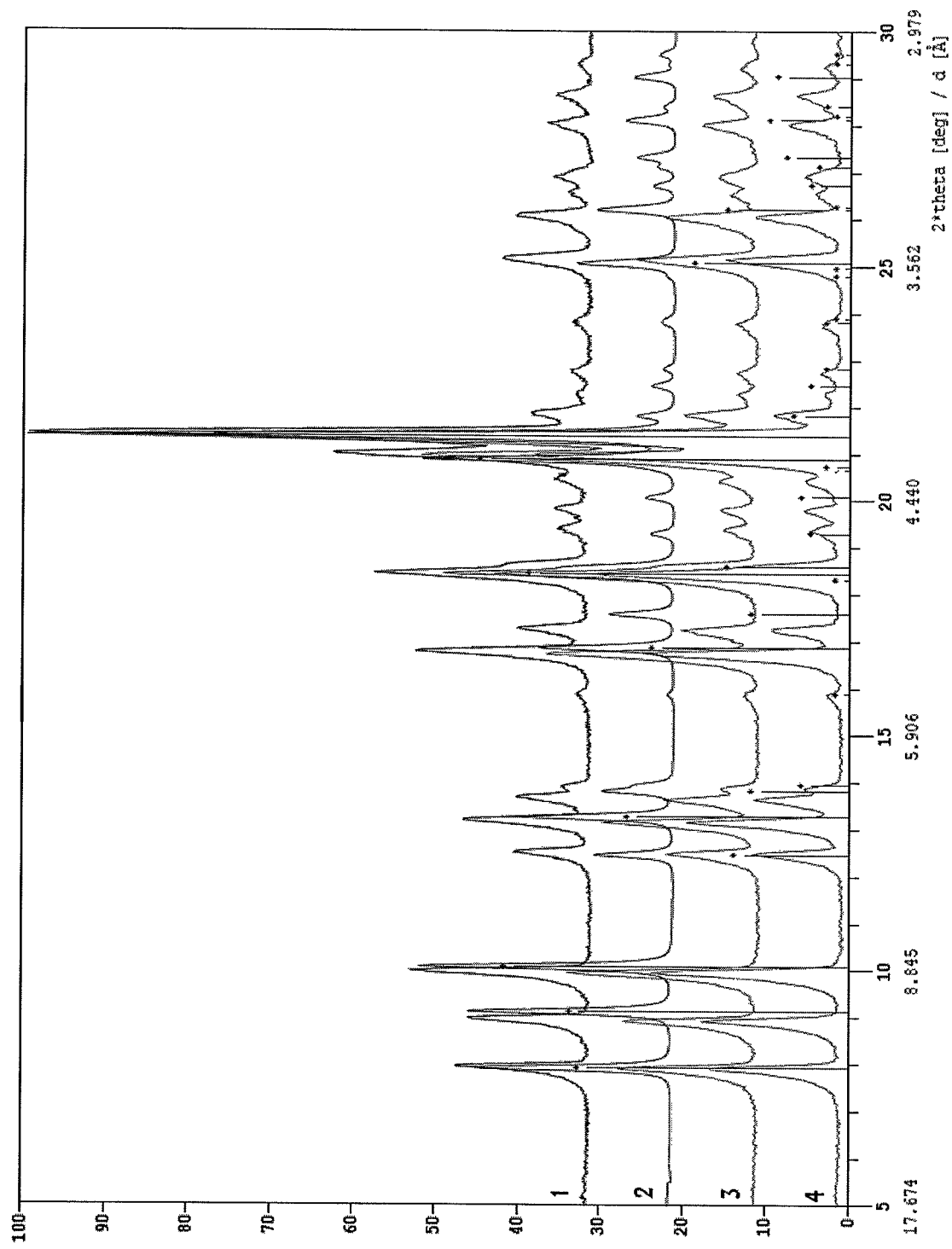
FIG. 5 shows the comparison of X-ray powder diffraction patterns of different crystalline 2'-O-fucosyllactose polymorph I samples. 1: Example A, item 1; 2: calculated diffractogram from polymorph I single crystal; 3: Example D; 4: Example C.

The XRPD patterns of crystalline 2'-O-fucosyllactose polymorph I having different α/β ratios and the simulated powder pattern of the single crystal are identical to each other showing that the different samples belong to the one and same crystalline polymorph (see FIG. 5).

Figure 8:
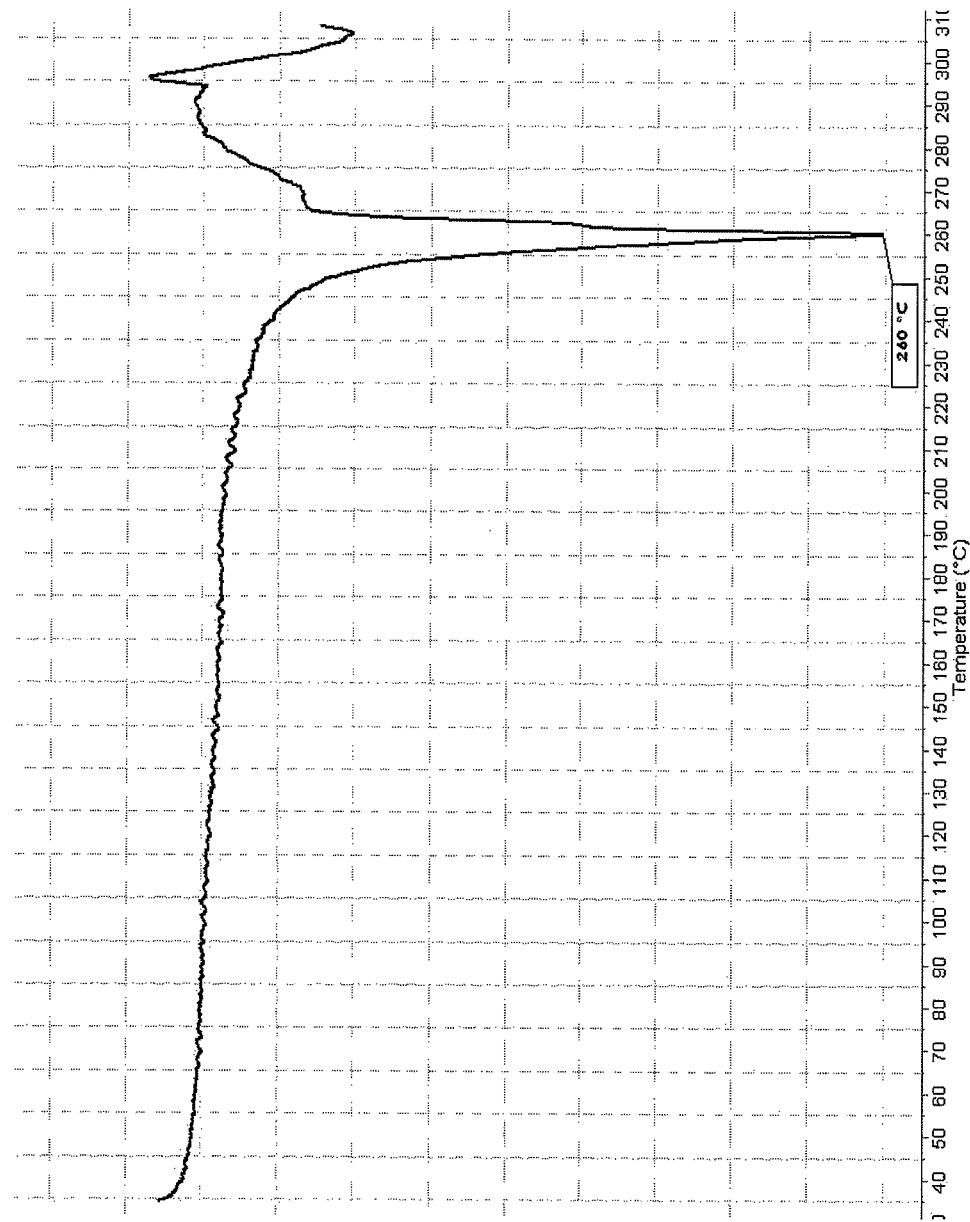
FIG. 8 shows the DSC thermogram of crystalline 2'-O-fucosyllactose polymorph I according to example A, item 1.
Figure 9:
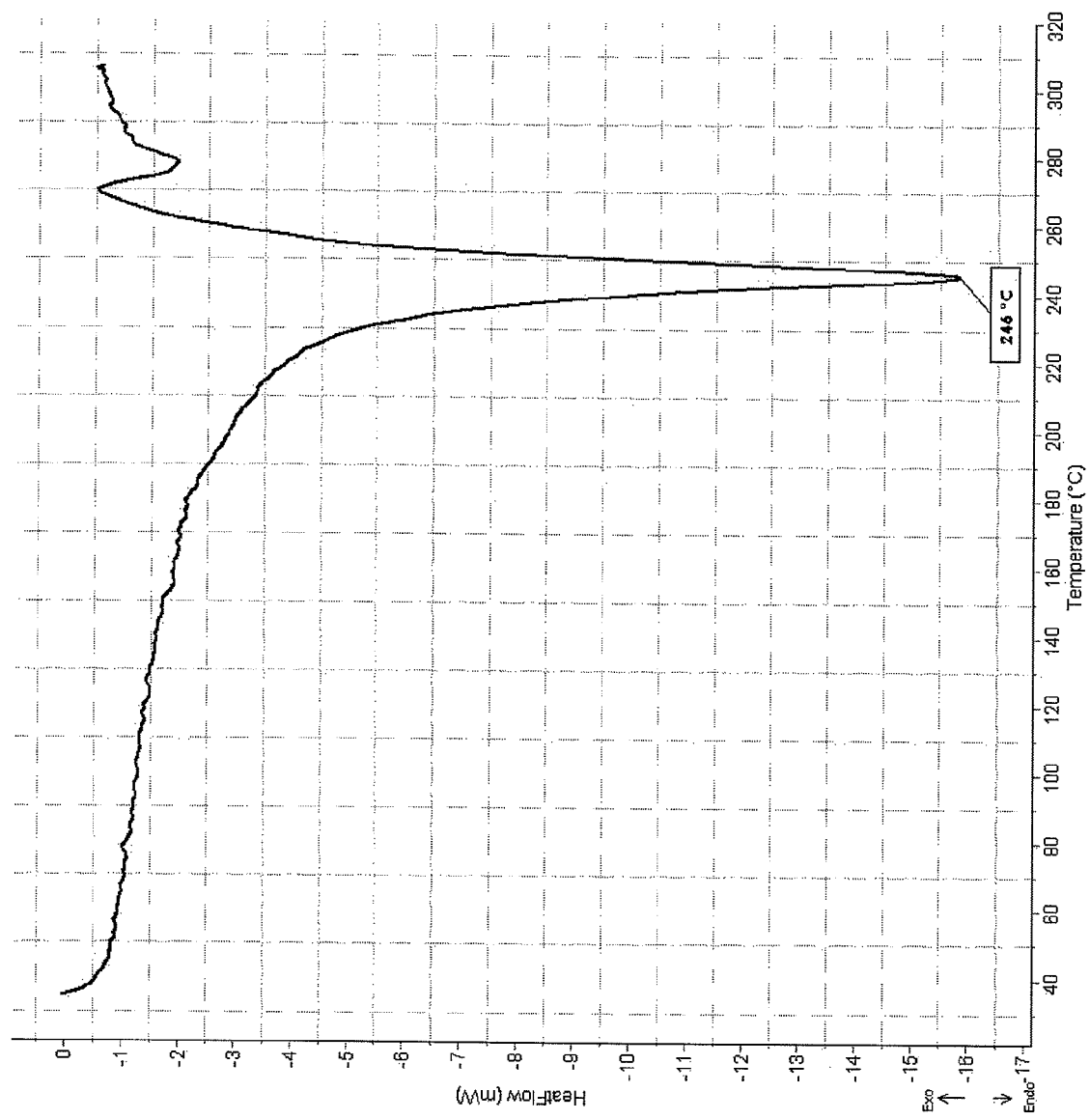
FIG. 9 shows the DSC thermogram of crystalline 2'-O-fucosyllactose polymorph I according to example C.

Crystalline 2'-O-fucosyllactose polymorph I containing 20±3% of β-anomer displays, in DSC investigations, an endothermic reaction with a peak maximum at 260±5° C., more preferably at 260±4° C., even more preferably at 260±3° C., most preferably at 260±2° C., in particular at 260±1° C. (see FIG. 8). Crystalline 2-FL sample having 12±3% of β-anomer shows an endothermic peak maximum at 246±5° C., more preferably at 246±4° C., even more preferably at 246±3° C., most preferably at 246±2° C., in particular at 246±1° C. (see FIG. 9).

Preferably the crystalline 2-FL polymorph I is substantially free from organic solvent and/or water. The expression "substantially free from organic solvent and/or water" intends to mean that the content of organic solvent(s) and/or water is at most 1000 ppm, preferably at most 800 ppm, more preferably at most 600 ppm, most preferably at most 400 ppm and in particular at most 200 ppm.

According to another preferred embodiment the crystalline 2-FL polymorph I is substantially pure. The expression "substantially pure" intends to mean that the crystalline 2-FL polymorph I contains less than 10 w/w % of impurity, preferably less than 5 w/w % of impurity, more preferably less than 1 w/w % of impurity, most preferably less than 0.5 w/w % of impurity, in particular less than 0.1 w/w % of impurity, wherein "impurity" refers to any physical entity different to the crystalline 2-FL polymorph I, such as amorphous 2-FL, different 2-FL polymorph(s), unreacted intermediate(s) remained from the synthesis of 2-FL, by-product(s), degradation product(s), inorganic salt(s) and/or other contaminations different to organic solvent(s) and/or water.

In order to perform comparative studies huge effort was allocated and many attempts were carried out to obtain crystalline 2-FL according to the literature method, but the procedures have not worked and the present inventors have never been able to reproduce the methods described by Kuhn. In addition, methods comprising steps such as "prolonged" storage or storage for "several" weeks do not hold out much hopes of reproduction. However, the inventors of the present application were able to produce crystalline 2-FL polymorphs.

Thus the present invention provides a process for preparing crystalline 2-FL polymorph I by crystallization from a solvent system containing one or more $C_1$-$C_3$ alcohols and optionally water in the absence of seed crystals. Term "$C_1$-$C_3$ alcohol" refers to mono- or dihydroxy alkanes having 1 to 3 carbon atoms, that is methanol, ethanol, n-propanol, i-propanol, ethylene glycol, 1,2-propanediol and 1,3-propanediol, preferably monohydroxy alkanes having 1 to 3 carbon atoms, more preferably methanol or ethanol. According to another preferred embodiment the solvent system may further contain water. The water content in the overall volume of the solvent system may preferably range up to 30 v/v %, more preferably up to 15 v/v %, most preferably up to 5 v/v %.

In a preferred realization 2-FL to be crystallized is dissolved in hot (5-10° C. less than boiling temperature) or boiling aqueous alcohol(s), then to this mixture hot or boiling same or different alcohol(s) is/are added gradually. The solution is allowed to cool to room temperature (rt) and the stirring is continued for 12-24 h. The precipitated crystals are collected by filtration and washed with cold solvent(s). Especially favoured alcohols are methanol and methanol/ethanol mixture.

According to another preferred embodiment, 2-FL to be crystallized is dissolved in hot or boiling alcohol(s), then to this mixture hot or boiling same or different alcohol(s) containing water is/are added gradually. The solution is allowed to cool to it and the stirring is continued for 12-24 h. The precipitated crystals are collected by filtration and washed with cold solvent(s). Especially favoured alcohols are methanol and methanol/ethanol mixture.

In a further preferred process 2-FL to be crystallized is dissolved in hot or boiling aqueous alcohol(s), then to this mixture hot or boiling same or different alcohol(s) containing water is/are added gradually. The solution is allowed to cool to it and the stirring is continued for 12-24 h. The precipitated crystals are collected by filtration and washed with cold solvent(s). Especially favoured alcohols are methanol and methanol/ethanol mixture.

According to a further preferred embodiment 2-FL in aqueous methanol, obtained in catalytic hydrogenolysis of benzylated 2-FL described in the international applications WO 2010/115934 or WO 2010/115935, is diluted with ethanol or isopropanol and the solution is allowed to stand and crystallize.

More preferably, O-(2-O-benzyl-α-L-fucopyranosyl)-(1→2)-O-(β-D-galactopyranosyl)-(1→4)-D-glucose (see international application WO 2010/115935) is subjected to catalytic hydrogenolysis in methanol in the presence of an acid such as cc. HCl. Before filtration of the catalyst the acid may be neutralized by a base, optionally in the form of an aqueous solution of the base, the solvents are evaporated partially and water is optionally added to the methanolic concentrate, then the solution is stirred or allowed to stand and crystallize.

The present invention provides another process for producing the crystalline 2-FL polymorph I, characterized in that the crystallization is carried out from a solvent system containing one or more $C_1$-$C_6$ alcohols and optionally water in the presence of seed crystals of polymorph I. Term "$C_1$-$C_6$ alcohol" refers to mono- or dihydroxy alkanes having 1 to 6 carbon atoms, such as methanol, ethanol, n-propanol, i-propanol, n-butanol, i-butanol, s-butanol, t-butanol, amylalcohol, n-hexanol ethylene glycol, propylene glycol, etc. Preferred $C_1$-$C_6$ alcohols are $C_1$-$C_6$ monohydroxy-alkanes, more preferably $C_1$-$C_4$ monohydroxy-alkanes such as methanol, ethanol, n-propanol, i-propanol, n-butanol, i-butanol, s-butanol and t-butanol. An even more preferred solvent system contains methanol, ethanol, n-propanol, i-propanol or mixtures thereof, in particular methanol or methanol/isopropanol.

In a preferred embodiment 2-FL to be crystallized is dissolved in hot (5-10° C. less than boiling temperature) or boiling alcohol under agitation until a clear solution is obtained. This solution is allowed to cool to rt, seed crystals of polymorph I are added and the stirring is continued for 12-24 h. The precipitated crystals are collected by filtration and washed with the cold solvent.

In another preferred realization 2-FL to be crystallized is dissolved in hot or boiling alcohol under agitation, then to this mixture hot or boiling another alcohol(s) is/are added gradually until a clear solution is obtained. This solution is allowed to cool to rt, seed crystals of polymorph I are added and the stirring is continued for 12-24 h. The precipitated crystals are collected by filtration and washed with the cold solvent.

According to another preferred example the solvent system further contains water. The water content in the overall volume of the solvent system may range up to 30 v/v %, preferably up to 20 v/v %, more preferably up to 10 v/v %.

In an especially preferred realization 2-FL to be crystallized is dissolved in hot (5-10° C. less than boiling temperature) or boiling aqueous alcohol(s), then to this mixture hot or boiling same or different alcohol(s) is/are added gradually. The solution is allowed to cool to rt, seed crystals of polymorph I are added and the stirring is continued for 12-24 h. The precipitated crystals are collected by filtration and washed with cold solvent(s). Especially favoured alcohols are methanol, ethanol and methanol/isopropanol mixture.

According to another preferred embodiment, 2-FL to be crystallized is dissolved in hot or boiling alcohol(s), then to this mixture hot or boiling same or different alcohol(s) containing water is/are added gradually. The solution is allowed to cool to rt, seed crystals of polymorph I are added and the stirring is continued for 12-24 h. The precipitated crystals are collected by filtration and washed with cold solvent(s). Especially favoured alcohols are methanol, ethanol and methanol/isopropanol mixture.

In a further preferred process 2-FL to be crystallized is dissolved in hot or boiling aqueous alcohol(s), then to this mixture hot or boiling same or different alcohol(s) containing water is/are added gradually. The solution is allowed to cool to rt, seed crystals of polymorph I are added and the stirring is continued for 12-24 h. The precipitated crystals are collected by filtration and washed with cold solvent(s). Especially favoured alcohols are methanol, ethanol and methanol/isopropanol mixture.

2-FL in amorphous solid form might be prepared by procedures described in the international applications WO 2010/115934 or WO 2010/115935.

In another aspect of the present invention crystalline 2'-O-fucosyllactose polymorph II comprises X-ray powder diffraction reflections, based on a measurement using CuKα radiation, at 16.98±0.20, 13.65±0.20 and 18.32±0.20 2Θ angles, more preferably at 16.98±0.20, 13.65±0.20, 18.32±0.20 and 21.70±0.20 2Θ angles, even more preferably at 16.98±0.20, 13.65±0.20, 18.32±0.20, 21.70±0.20 and 15.22±0.20 2Θ angles, most preferably at 16.98±0.20, 13.65±0.20, 18.32±0.20, 21.70±0.20, 15.22±0.20 and 20.63±0.20 2Θ angles, in particular at 16.98±0.20, 13.65±0.20, 18.32±0.20, 21.70±0.20, 15.22±0.20, 20.63±0.20 and 11.94±0.20 2Θ angles. List of peaks of the XRPD pattern of crystalline 2'-O-fucosyllactose polymorph II is reported in Table 3.

TABLE 3

List of peaks of the XRPD pattern of crystalline 2'-O-fucosyllactose polymorph II

| 2Θ | rel. |
|---|---|
| 7.89 | 7 |
| 9.14 | 12 |
| 9.81 | 8 |
| 10.0 | 6 |
| 10.38 | 3 |
| 10.68 | 1 |
| 11.73 | 18 |
| 11.94 | 34 |
| 12.17 | 20 |
| 12.48 | 2 |
| 13.23 | 6 |
| 13.65 | 89 |
| 14.12 | 26 |
| 15.22 | 68 |
| 15.86 | 18 |
| 16.29 | 4 |
| 16.98 | 100 |
| 17.32 | 35 |
| 18.12 | 35 |
| 18.32 | 85 |
| 18.96 | 33 |
| 19.29 | 26 |
| 19.70 | 19 |
| 19.80 | 19 |
| 20.11 | 13 |
| 20.63 | 40 |
| 21.44 | 25 |
| 21.70 | 67 |
| 21.93 | 20 |
| 22.29 | 10 |
| 22.58 | 13 |
| 23.16 | 7 |
| 23.55 | 16 |
| 23.83 | 16 |
| 24.04 | 16 |
| 24.60 | 11 |
| 24.87 | 11 |
| 25.33 | 33 |
| 25.80 | 32 |
| 26.12 | 10 |
| 26.79 | 11 |
| 27.46 | 5 |
| 27.62 | 5 |
| 28.00 | 6 |
| 28.61 | 10 |
| 28.94 | 4 |
| 29.25 | 5 |
| 29.64 | 7 |
| 30.43 | 9 |
| 30.68 | 7 |
| 31.67 | 16 |
| 32.24 | 5 |
| 32.74 | 8 |
| 32.94 | 5 |
| 33.32 | 7 |
| 33.70 | 9 |

TABLE 3-continued

List of peaks of the XRPD pattern of crystalline
2'-O-fucosyllactose polymorph II

| 2Θ | rel. |
|---|---|
| 33.92 | 6 |
| 34.32 | 10 |
| 34.55 | 8 |
| 35.07 | 6 |
| 35.65 | 7 |
| 35.78 | 5 |
| 36.05 | 4 |
| 36.41 | 14 |
| 36.50 | 14 |
| 36.60 | 12 |
| 37.18 | 10 |
| 37.61 | 8 |
| 38.25 | 9 |
| 38.48 | 7 |
| 39.68 | 8 |

Figure 12:
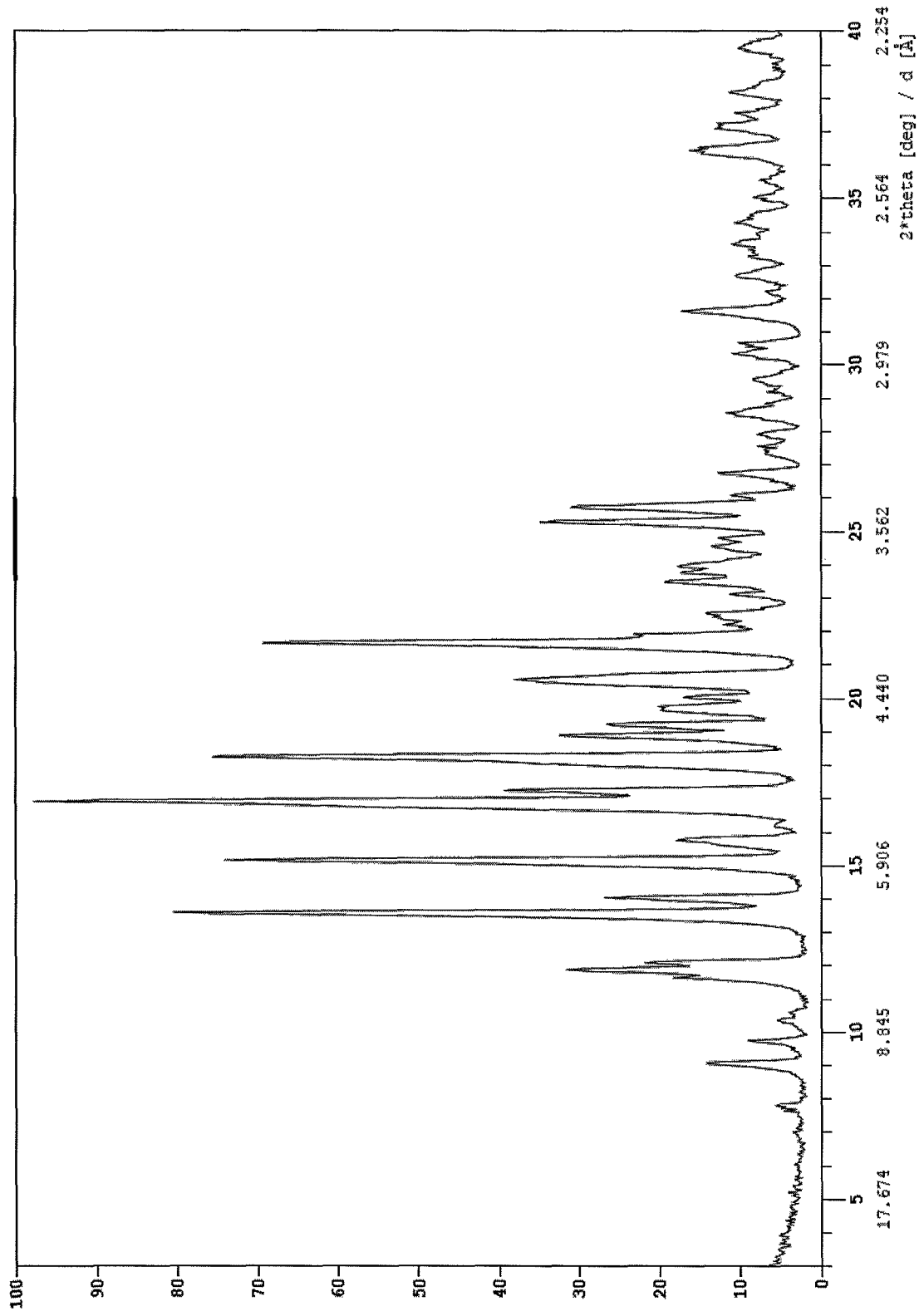
FIG. 12 shows the X-ray powder diffraction pattern of 2'-O-fucosyllactose polymorph II according to example E.
Figure 13:
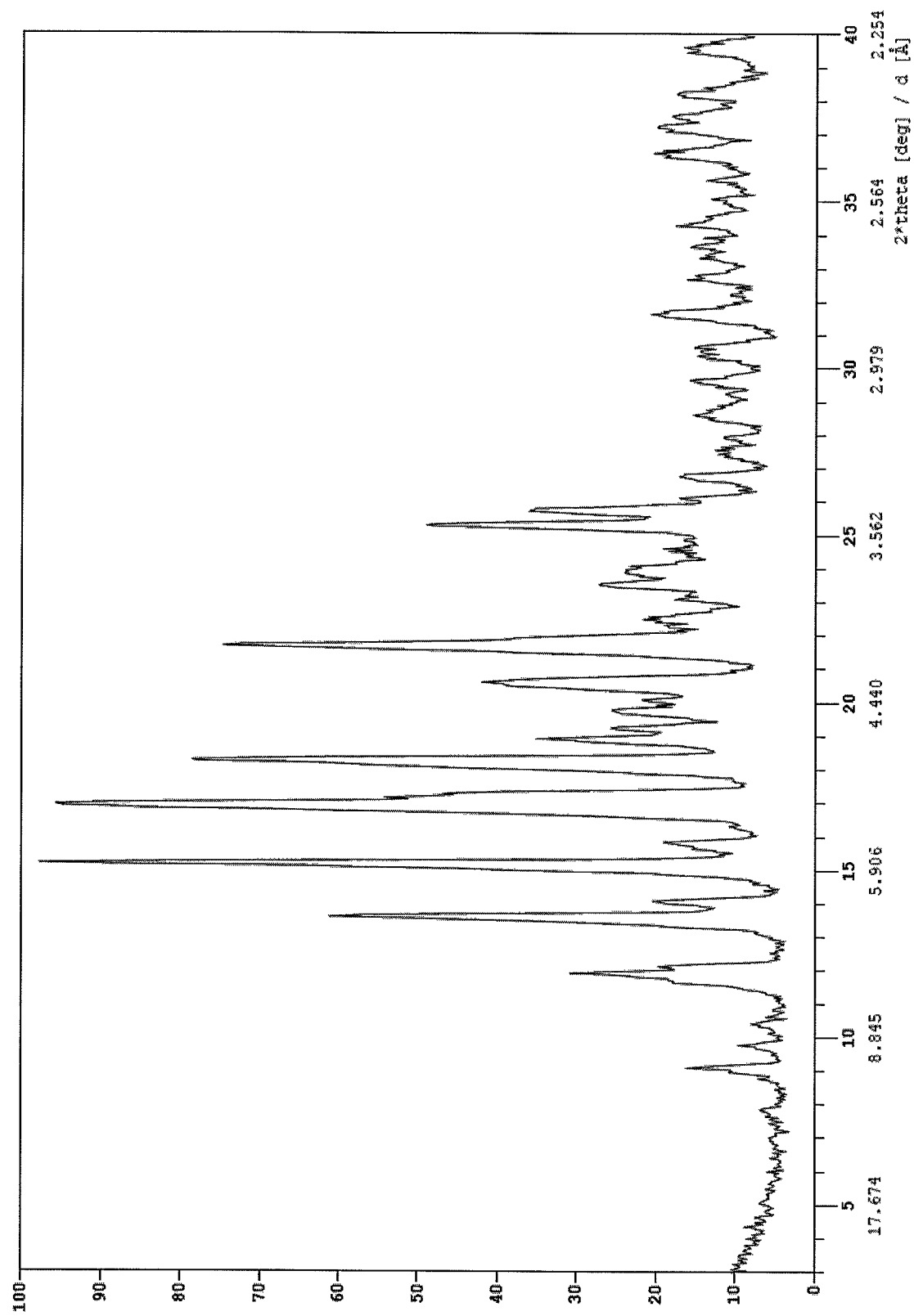
FIG. 13 shows the X-ray powder diffraction pattern of 2'-O-fucosyllactose polymorph II according to example F.
Figure 14:
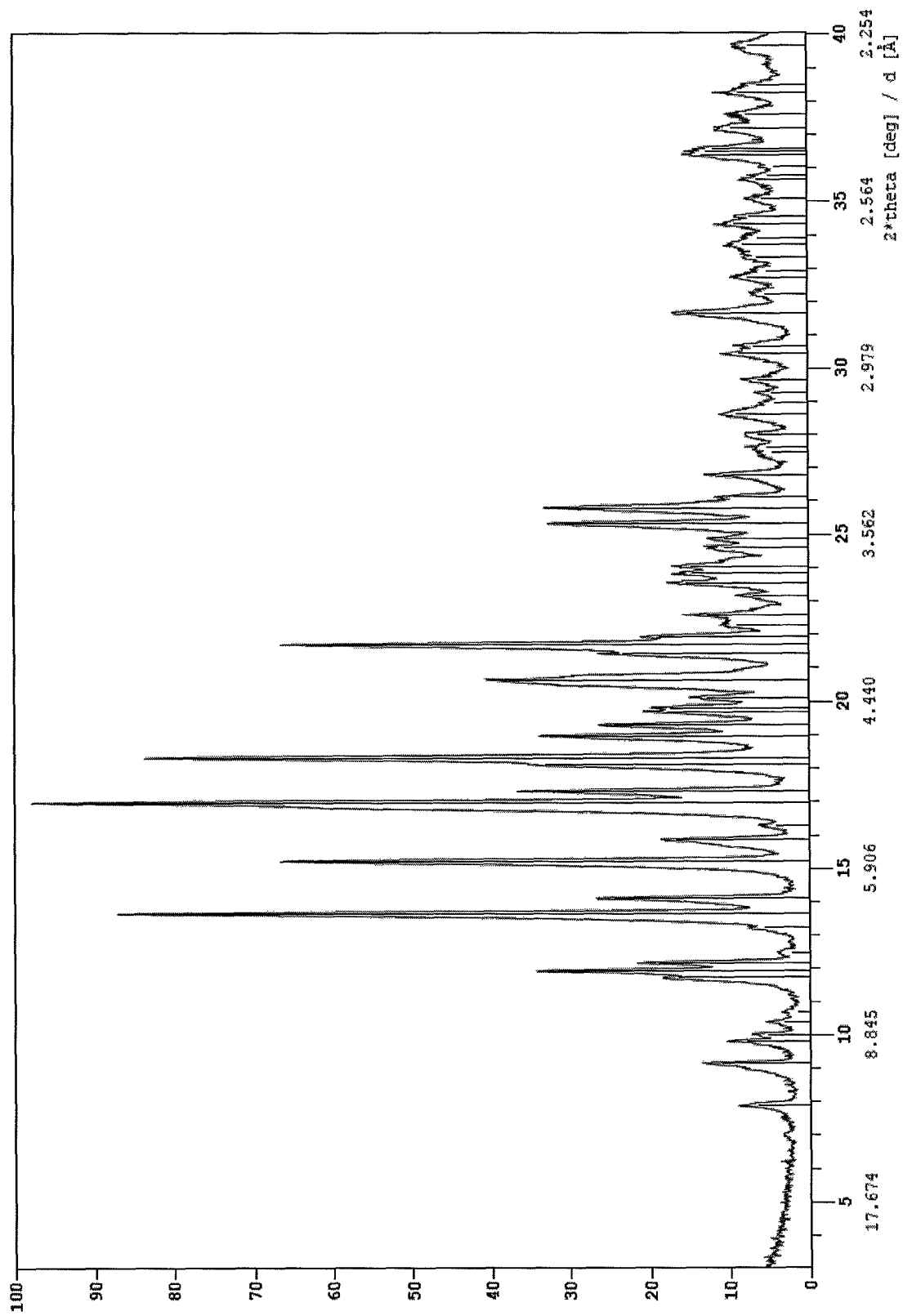
FIG. 14 shows X-ray powder diffraction pattern of 2'-O-fucosyllactose polymorph II according to example G.

The XRPD patterns of different samples of crystalline 2'-O-fucosyllactose polymorph II are shown in FIGS. 12-14.

Crystalline 2'-O-fucosyllactose polymorph II according to the present invention has a characteristic IR peak at 3571±4 cm$^{-1}$, preferably has characteristic IR peaks at 3571±4 and 1042±4 cm$^{-1}$, more preferably at 3571±4, 1042±4 and 1412±4 cm$^{-1}$, even more preferably at 3571±4, 1042±4, 1412±4 and 1255±4 cm$^{-1}$, in particular at 3571±4, 964±4, 1042±4, 1072±4, 1124±4, 1154±4, 1255±4, 1295±4, 1342±4, 1412±4, 2877±4, 2906±4, 2956±4, 3333±4 and 3442±4 cm$^{-1}$.

Figure 17:
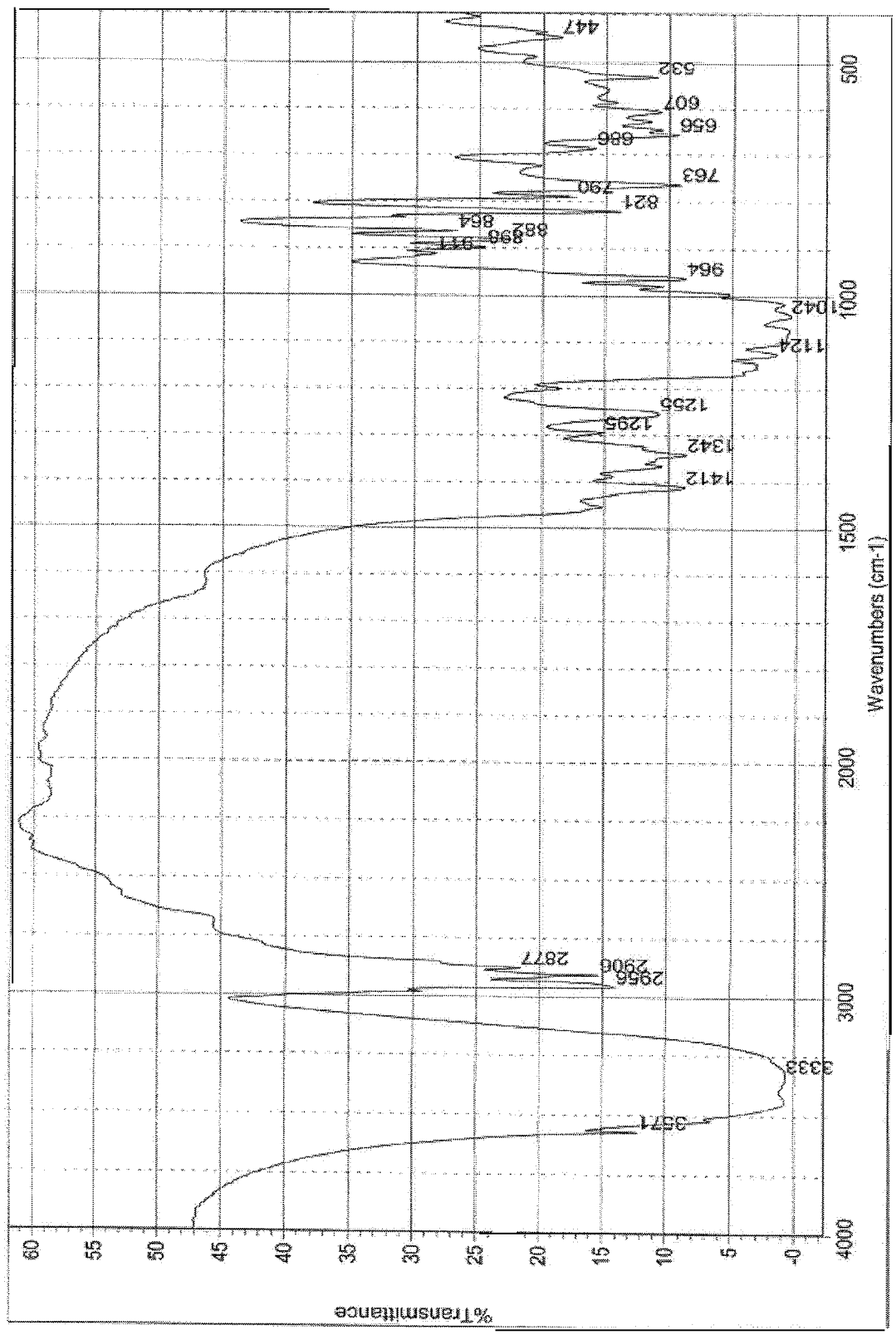
FIG. 17 shows the IR spectrum of 2'-O-fucosyllactose polymorph II.

The IR spectrum of 2-FL polymorph II is shown in FIG. 17.

The crystalline 2-FL polymorph II can be considered as an anomeric mixture of α- and β-anomers or even pure form of one of the anomers. No constitutional water and/or solvent are incorporated in the crystal structure.

Figure 15:
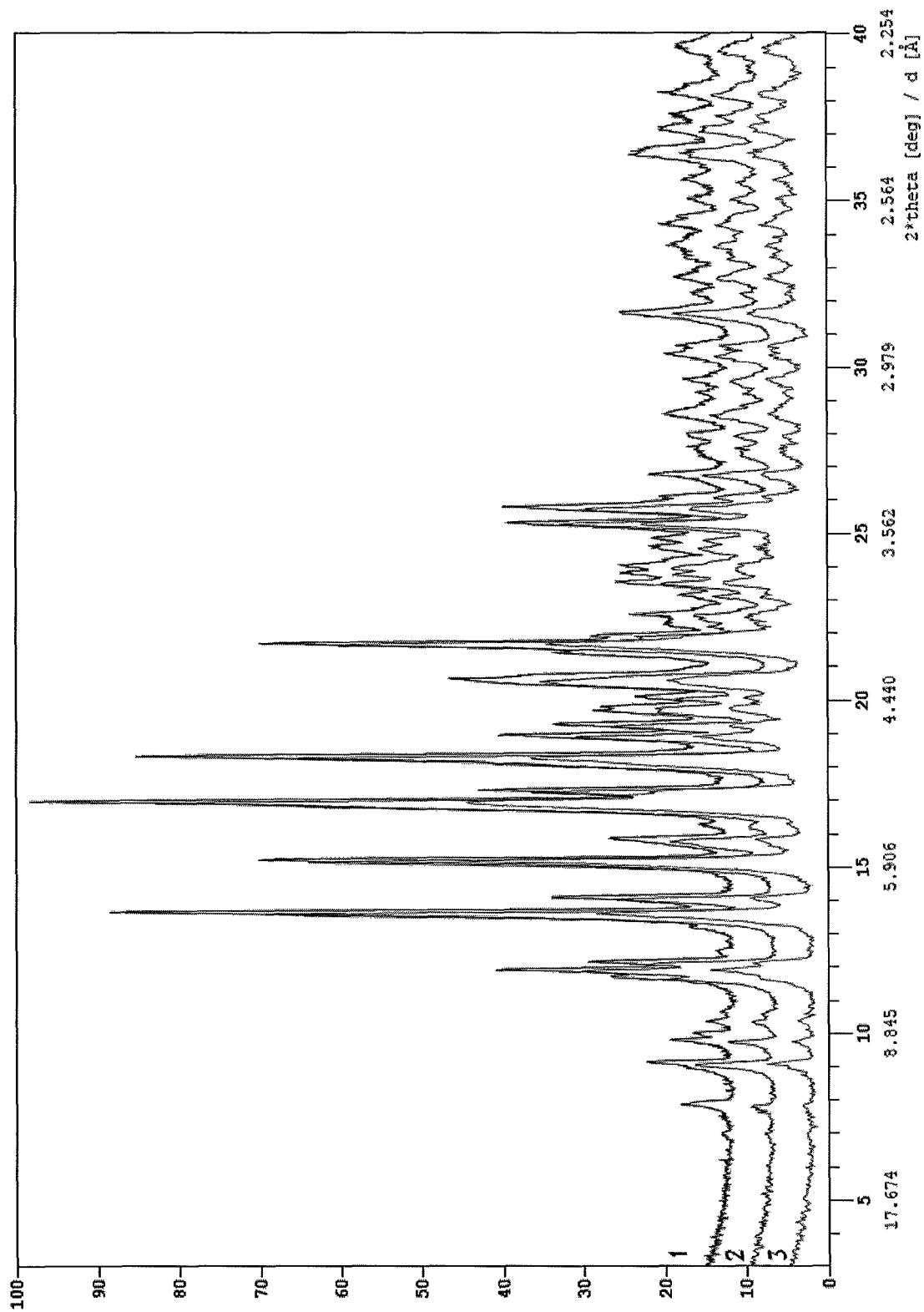
FIG. 15 shows the comparison of X-ray powder diffraction patterns of different crystalline 2'-O-fucosyllactose polymorph II samples. 1: Example G; 2: Example E; 3: Example F.

The XRPD patterns of crystalline 2'-O-fucosyllactose polymorph II obtained under different conditions are identical to each other showing that the different samples belong to the one and same crystalline polymorph (see FIG. 15).

Figure 18:
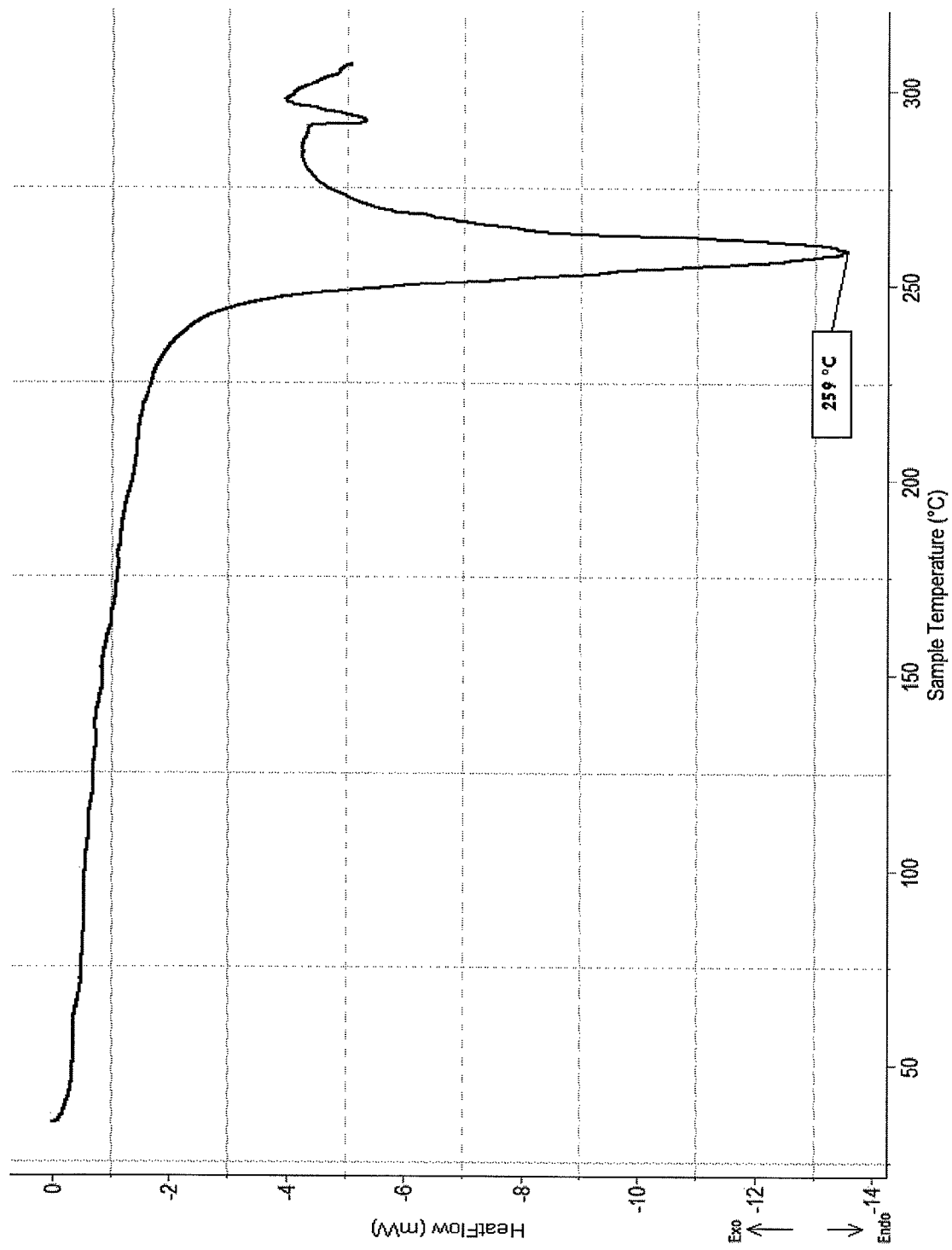
FIG. 18 shows the DSC thermogram of 2'-O-fucosyllactose polymorph II according to example E.
Figure 19:
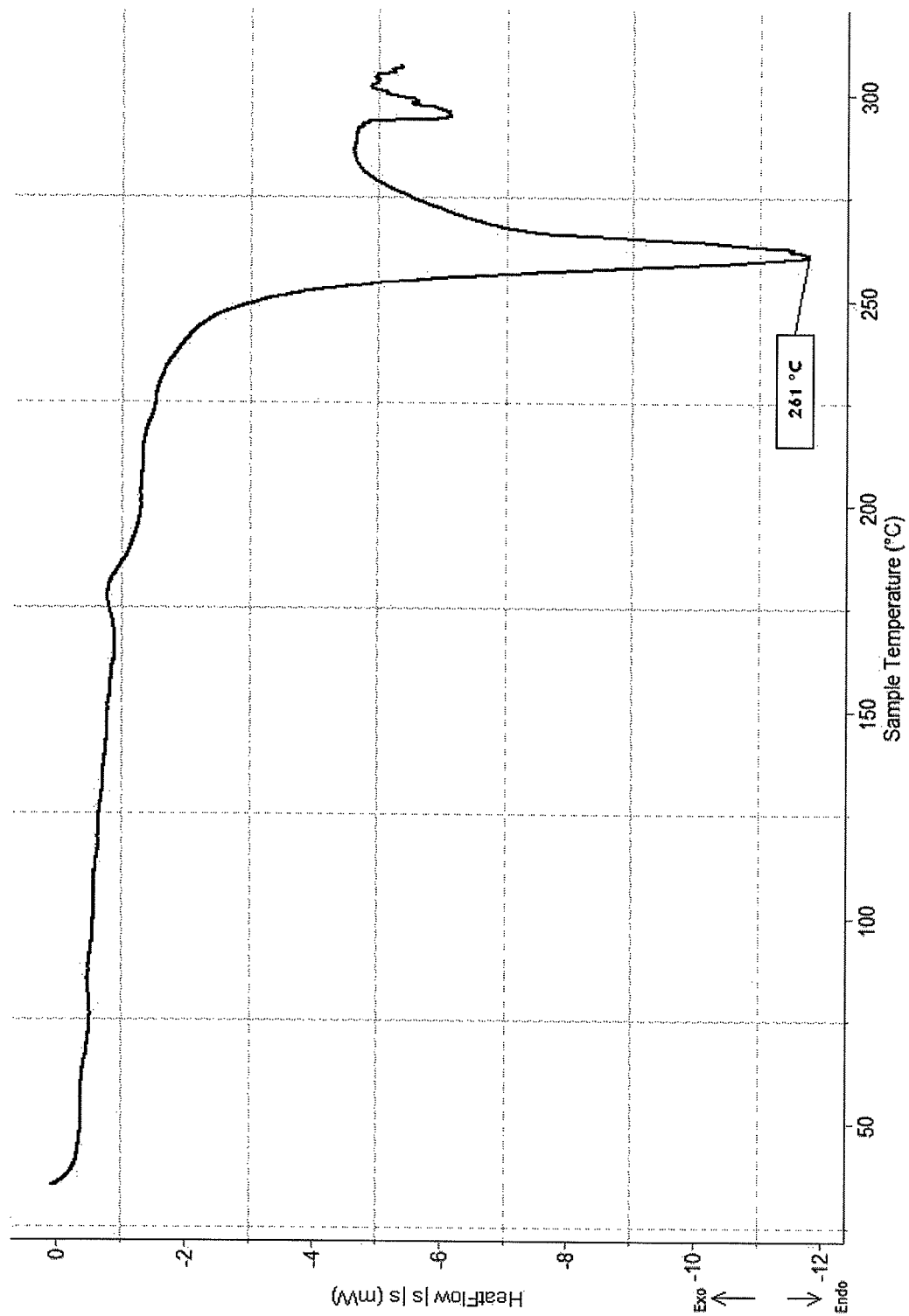
FIG. 19 shows the DSC thermogram of 2'-O-fucosyllactose polymorph II according to example F.
Figure 20:
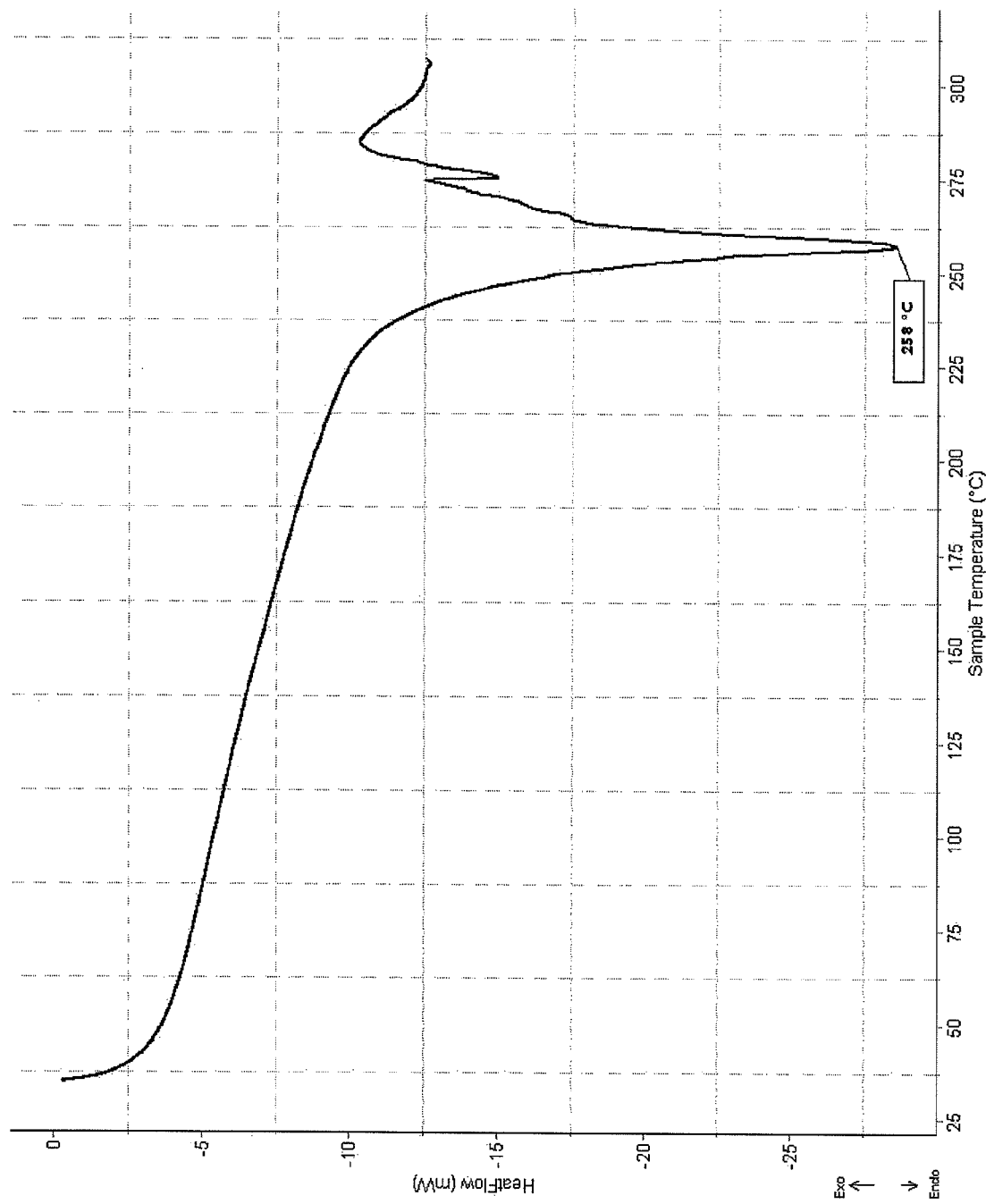
FIG. 20 shows the DSC thermogram of 2'-O-fucosyllactose polymorph II according to example G.

Crystalline 2'-O-fucosyllactose polymorph II displays, in DSC investigations, an endothermic reaction with a peak maximum at 259.5±5° C., more preferably at 259.5±4° C., even more preferably at 259.5±3° C., most preferably at 259.5±2° C. (see FIGS. 18-20).

Preferably, the crystalline 2-FL polymorph II is substantially free from organic solvent and/or water. The expression "substantially free from organic solvent and/or water" intends to mean that the content of organic solvent(s) and/or water is at most 1000 ppm, preferably at most 800 ppm, more preferably at most 600 ppm, most preferably at most 400 ppm and in particular at most 200 ppm.

According to another preferred embodiment the crystalline 2-FL polymorph II is substantially pure. The expression "substantially pure" intends to mean that the crystalline 2-FL polymorph II contains less than 10 w/w % of impurity, preferably less than 5 w/w % of impurity, more preferably less than 1 w/w % of impurity, most preferably less than 0.5 w/w % of impurity, in particular less than 0.1 w/w % of impurity, wherein "impurity" refers to any physical entity different to crystalline 2-FL polymorph II, such as amorphous 2-FL, different 2-FL polymorph(s), unreacted intermediate(s) remained from the synthesis of 2-FL, by-product(s), degradation product(s), inorganic salt(s) and/or other contaminations different to organic solvent(s) and/or water.

The present invention provides method for producing the crystalline 2-FL polymorph II, characterized in that the crystallization is carried out from a solvent system comprising one or more $C_1$-$C_6$ alcohols in the presence of seed crystals of polymorph II. Term "$C_1$-$C_6$ alcohol" refers to mono- or dihydroxy alkanes having 1 to 6 carbon atoms, such as methanol, ethanol, n-propanol, i-propanol, n-butanol, i-butanol, s-butanol, t-butanol, amylalcohol, n-hexanol ethylene glycol, propylene glycol, etc. Preferred $C_1$-$C_6$ alcohols are $C_1$-$C_6$ monohydroxy-alkanes, more preferably $C_1$-$C_4$ monohydroxy-alkanes such as methanol, ethanol, n-propanol, i-propanol, n-butanol, i-butanol, s-butanol and t-butanol. An even more preferred solvent system comprises methanol, ethanol, n-propanol, i-propanol or mixtures thereof, in particular methanol.

In a preferred embodiment 2-FL to be crystallized is dissolved in hot (5-10° C. less than boiling temperature) or boiling alcohol under agitation until a clear solution is obtained. This solution is allowed to cool to rt, seed crystals of polymorph II are added and the stirring is continued for 12-24 h. The precipitated crystals are collected by filtration and washed with the cold solvent.

According to another preferred example the solvent system further contains water. The water content in the overall volume of the solvent system may range up to 60 v/v %, preferably up to 55 v/v %, more preferably between 40-55 v/v %.

In an especially preferred realization 2-FL to be crystallized is dissolved in hot (40-80° C.) aqueous alcohol. The solution is allowed to cool to rt, seed crystals of polymorph II are added and the stirring is continued for 12-24 h. The precipitated crystals are collected by filtration and washed with cold solvent(s). Especially favoured alcohol is methanol.

According to another method for producing the crystalline 2-FL polymorph II syrupy 2-FL, solid 2-FL comprising amorphous 2-FL or any 2-FL polymorph(s) different to polymorph II or mixture of amorphous 2-FL and any 2-FL polymorph(s) different to polymorph II is suspended in one or more less polar aprotic organic solvent and stirred for 6-72 hours. Optionally, the solid 2-FL to be (re)crystallized may also contain 2-FL polymorph II.

Less polar aprotic organic solvent means aprotic organic solvents having dielectric constant less than approx. 21. For example such typical solvents are esters, ketones, ethers, hydrocarbons and halogenated hydrocarbons.

Esters preferably mean esters of $C_1$-$C_6$ carboxylic acids with $C_1$-$C_6$ alcohols, more preferably esters of acetic acid with $C_1$-$C_6$ alcohols such as methyl acetate, ethyl acetate, n-propyl acetate, i-propyl acetate, n-butyl acetate, i-butyl acetate amyl acetate, hexyl acetate and the like.

Ketones preferably mean open chain or cyclic ketones with 3-6 carbon atoms, more preferably acetone or methyl ethyl ketone.

Ethers preferably mean open chain or cyclic ethers with 2-6 carbon atoms, more preferably diethyl ether, methyl t-butyl ether, THF or dioxane.

Hydrocarbons preferably means alkanes (linear or branched) or cycloalkanes having 5-7 carbon atoms, more preferably n-pentane, n-hexane or cyclohexane. Moreover hydrocarbons relate to aromatic hydrocarbons such as benzene, toluene and xylenes, as well.

Halogenated hydrocarbons mean hydrocarbons defined above substituted with one or more halogen atom selected from fluoro, chloro and bromo, more preferably dichloromethane, chloroform, tetrachloromethane, 1,2-dichloroethane or chlorobenzene.

In a preferred embodiment an ester type solvent is used as less polar aprotic solvent. In a more preferred embodiment the ester type solvent may further contain water. The water content in the overall volume of the solvent system may range up to 5 v/v %, preferably up to 2 v/v %, more preferably between 1-2 v/v %.

According to another preferred embodiment the suspension is stirred at a temperature within the range of 0° C. to reflux, preferably 20° C. to 80° C.

In an especially preferred embodiment ethyl acetate is the solvent of choice which may contain 1-2 v/v % of water. The suspension can be made using pure ethyl acetate or aqueous ethyl acetate. Alternatively the water may be added to the suspension continuously or sequentially. The suspension is then heated up slowly under stirring to 60-75° C., preferably 65-70° C. and kept at this temperature for 6-24 hours, preferably 10-14 hours.

Figure 16:
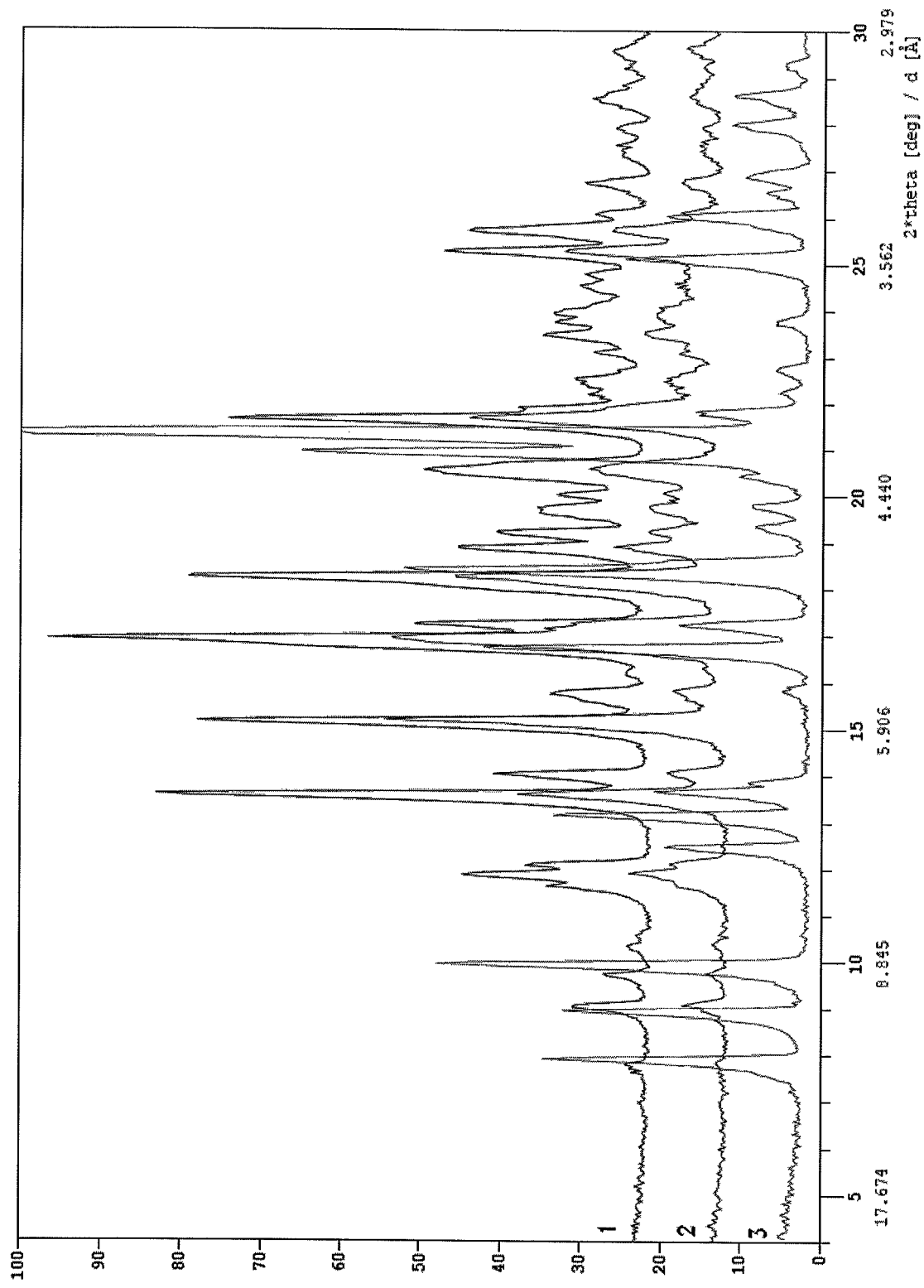
FIG. 16 shows the comparison of X-ray powder diffraction patterns of crystalline 2'-O-fucosyllactose polymorphs I and II. 1: Example E; 2: Example F; 3: Example A, item 1.

Crystalline 2-FL polymorph I and polymorph II, based on the evidence of their powder diffraction patterns, represent different crystalline modifications (see FIG. 16). Moreover, both crystalline modifications can be produced readily and a reproducible manner.

In a further embodiment crystalline 2-FL polymorph I and/or crystalline 2-FL polymorph II is suitable for pharmaceutical use. 2-FL acts as prophylactic and therapeutic agent that inhibits diseases caused by mucosal pathogens like *Campylobacter*, caliciviruses and rotavirus, which are responsible for diarrhoea especially in infants, or diseases caused by respiratory pathogens provoking pneumonia. Through its immunomodulatory effect 2-FL benefits the abnormal immune response found in some monocyte-mediated diseases. In humans and animals, by dosing with 2-FL it is possible to promote insulin secretion, suppress the elevation of a blood glucose level, ameliorate diabetes mellitus, promote growth and increase an insulin level in breast milk. Furthermore the combination of 2-FL with one or more *Bifidobacterium* species as probiotic(s) such as *Bifidobacterium lactis, Bifidobacterium infantis, Bifidobacterium breve* or *Bifidobacterium longum*, is suitable for use in the prevention of opportunistic infections in immune-compromised individuals.

In another aspect, the present invention provides pharmaceutical composition comprising crystalline 2'-O-fucosyllactose polymorph I and/or crystalline 2-FL polymorph II as active ingredient and one or more pharmaceutically acceptable carriers including but not limited to additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, syrups, injections, liquids, elixirs, extracts and tincture. Pharmaceutical compositions comprising crystalline 2-FL polymorph I and/or crystalline 2-FL polymorph II inhibits diseases caused by mucosal pathogens like *Campylobacter*, caliciviruses and rotavirus, which are responsible for diarrhoea especially in infants, or diseases caused by respiratory pathogens provoking pneumonia, influences the abnormal immune response found in some monocyte-mediated diseases, promotes insulin secretion, suppresses the elevation of a blood glucose level, ameliorates diabetes mellitus, promotes growth and increases an insulin level in breast milk The pharmaceutical composition comprising crystalline 2-FL polymorph I and/or crystalline 2-FL polymorph II and one or more *Bifidobacterium* species as probiotic(s) such as *Bifidobacterium lactis, Bifidobacterium infantis, Bifidobacterium breve* or *Bifidobacterium longum*, is suitable for use in the prevention of opportunistic infections in immune-compromised individuals.

In a further embodiment crystalline 2-FL polymorph I and/or crystalline 2-FL polymorph II is used for the preparation of pharmaceutical compositions. Pharmaceutical compositions can be manufacture by means of any usual manner known in the art, e.g. described in the most recent edition of Remington's Pharmaceutical Sciences, a standard reference text in the field.

In a further embodiment it is provided nutritional formulations comprising crystalline 2-FL polymorph I and/or crystalline 2-FL polymorph II such as foods, drinks or feeds. The nutritional formulation may contain edible micronutrients, vitamins and minerals as well. The amounts of such ingredient may vary depending on whether the formulation is intended for use with normal, healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolized cornstarch, etc.) and proteins from casein, soybean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formula may contain the following minerals and trace elements: Ca, P, K, Na, Cl, Mg, Mn, Fe, Cu, Zn, Se, Cr or I.

In a preferred embodiment the nutritional formulation is an infant formula. Infant formula means a foodstuff intended for particular nutritional use by infants during the first 4-6 months of life and satisfying by itself the nutritional requirements of infants. It may contain one or more probiotic *Bifidobacterium* species, prebiotics such as fructooligosaccharides and galactooligosaccharides, proteins from casein, soybean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula contains crystalline 2-FL polymorph I and/or crystalline 2-FL polymorph II in a total amount of 0.1-3.0 g/100 g formula.

In another preferred embodiment the nutritional formulation may be a food supplement including crystalline 2-FL polymorph I and/or crystalline 2-FL polymorph II. The food supplement may comprise one or more probiotics in an amount sufficient to achieve the desired effect in an individual, preferably in children and adults. The food supplement may also contain vitamins, minerals, trace elements and other micronutritients as well. The food supplement may be for example in the form of tablets, capsules, pastilles or a liquid. The supplement may contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc. The daily dose of 2-FL ranges from 0.1 to 3.0 g.

According to a more preferred embodiment the food supplement is digestive health functional food as the administration of 2-FL provides a beneficial effect on digestive health. Digestive health functional food is a processed food used with intention enhance and preserve digestive health by crystalline 2-FL polymorph I and/or crystalline 2-FL polymorph II as physiologically functional ingredient or component in forms of tablet, capsule, powder, etc. Different terms such as dietary supplement, nutraceutical, designed food, health product may also be used to refer to functional food.

In a further embodiment crystalline 2-FL polymorph I and/or crystalline 2-FL polymorph II is used for the preparation of nutritional formulation including foods, drinks and feeds, preferably infant formulas, food supplements and digestive health functional food. The nutritional formulation may be prepared in any usual manner. For example, it may be prepared by admixing micronutrient components in appropriate proportions. Then the vitamins and minerals are added, but to avoid thermal degradation or decomposition heat sensitive vitamins can be added after homogenization. Lipophilic vitamins may be dissolved in the fat source before mixing. A liquid mixture is formed using water, whose temperature is preferably about between 50-80° C. to help dissolution or dispersal of the ingredients. Crystalline 2-FL polymorph I and/or crystalline 2-FL polymorph II can be added at this stage. The resulting mixture is then homogenized by flash heating to about 80-150° C. by means of steam injection, heat exchanger or autoclave. This thermal treatment reduces significantly the bacterial loads as well. The hot mixture is then cooled rapidly to about 60-80° C. If needed, further homogenization may be carried out at this temperature under high pressure of about 2-30 MPa. After cooling heat sensitive constituents may be added at this stage, and the pH and the content of the solids are conveniently adjusted. The resulting mixture is then dried by conventional method such as spray drying or freeze drying to powder. Probiotics may be added at this point by dry-mixing.

Other features of the invention will become apparent in the course of the following descriptions of exemplary embodiments which are given for illustration of the invention and are not to be limiting thereof.

EXAMPLES

Crystallization Procedures

Polymorph I

A) Amorphous 2-FL was dissolved in a first hot or boiling solvent and optionally a second hot or boiling solvent was added gradually under stirring. The solution was allowed to cool to rt, optionally seeded with polymorph I and the stirring was continued for 12-24 h. The precipitated crystals were collected by filtration, washed with cold solvent(s) and dried. The solvent used are listed in the table below. The yields range 63-90%.

| item | first solvent | second solvent | seeding |
|---|---|---|---|
| 1. | hot 80% aqueous methanol (1 volume) | boiling methanol (2 volumes) | no |
| 2. | hot 80% aqueous methanol (1 volume) | boiling methanol (2 volumes) | yes |
| 3. | boiling methanol (2 volumes) | — | yes |
| 4. | boiling methanol (5 volumes) | hot isopropanol (2.5 volumes) | yes |

Figure 10:
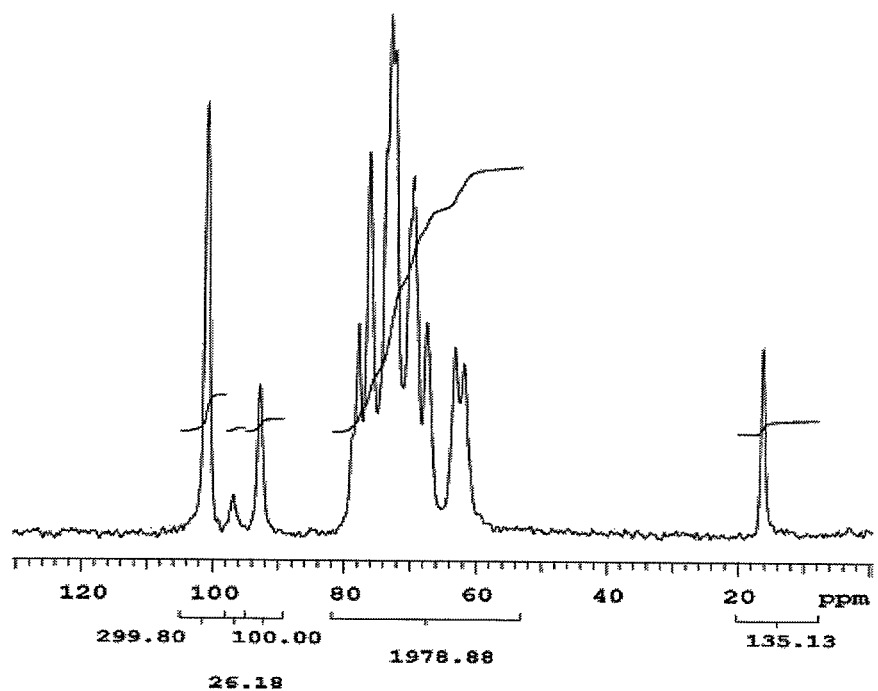
FIG. 10 shows the solid-state $^{13}$C-NMR spectrum of 2'-O-fucosyllactose polymorph I according to example A, item 1.

The sample according to item 1 contains 20±3% of β-anomer according to solid-state $^{13}$C-NMR measurement (see FIG. 10).

B) 10.0 g of O-(2-O-benzyl-α-L-fucopyranosyl)-(1→2)-O-(β-D-galactopyranosyl)-(1→4)-D-glucose in methanol (40 ml) and water (6.5 ml) were subjected to catalytic hydrogenation in the presence of 10% palladium on charcoal (850 mg) according to the international application WO 2010/115635. After removing the catalyst by filtration the filtrate was diluted with 2.5-fold volume of ethanol compared to the filtrate. The solution was allowed to stand at it for 2 days and the crystals precipitated were collected.

Figure 11:
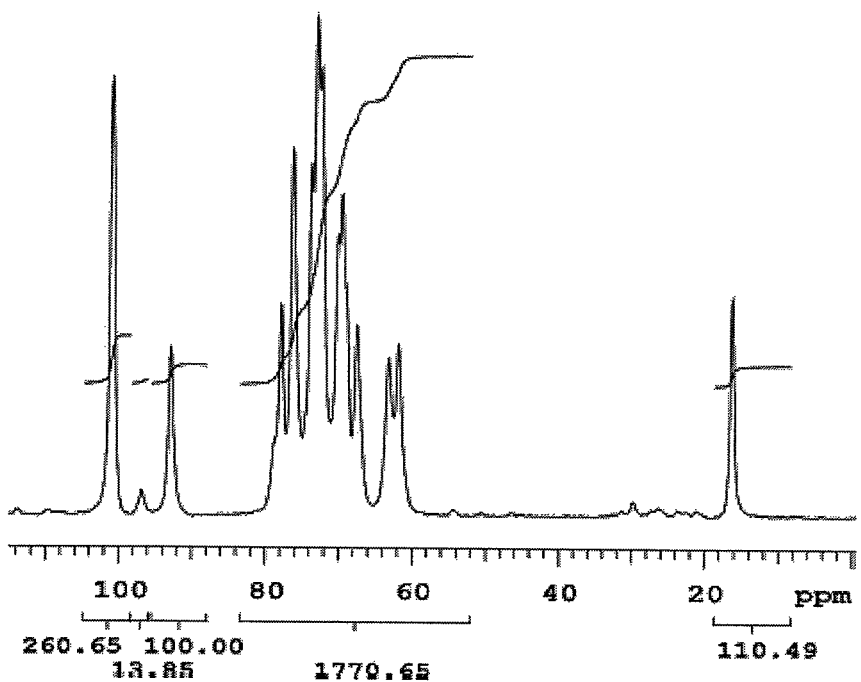
FIG. 11 shows the solid-state $^{13}$C-NMR spectrum of 2'-O-fucosyllactose polymorph I according to example C.

C) O-(2-O-Benzyl-α-L-fucopyranosyl)-(1→2)-O-(β-D-galactopyranosyl)-(1→4)-D-glucose (200 g) was dissolved in methanol (1200 ml) and cc. HCl solution (4 ml) in methanol (200 ml) was added. After addition of a slurry of 10% Pd/C (10 g) in methanol (100 ml), the mixture was stirred under hydrogen atmosphere at rt and 3-3.5 bar for 1 hour. The catalyst was filtered off and washed with methanol, the filtrate was concentrated to a solution that weights approx. 600 g, then 10 ml of water was added. Crystals precipitate under stirring which were collected by filtration, washed with methanol and dried to yield 113 g of product (67%). The sample contains 12±3% of β-anomer according to solid-state $^{13}$C-NMR measurement (see FIG. 11).

D) O-(2-O-Benzyl-α-L-fucopyranosyl)-(1→2)-O-(β-D-galactopyranosyl)-(1→4)-D-glucose (200 g) was dissolved in methanol (1400 ml) and cc. HCl solution (4 ml) was added. After addition of a slurry of 10% Pd/C (10 g) in methanol (100 ml), the mixture was stirred under hydrogen atmosphere at it and 3, 5-4 bar for 1 hour. The reaction mixture was neutralized with sodium carbonate (2.0 g in 30 ml of methanol), then the catalyst was filtered off and washed with methanol, the filtrate was concentrated to a solution that weights approx. 600 g, then 10 ml of water was added. Crystals precipitate under stirring which were collected by filtration, washed with methanol and dried to yield 102 g of product (61%).

Polymorph II

E) Amorphous 2-FL (50 g) was dissolved in mixture of methanol (25 ml) and water (30 ml) and heated to 76° C. The solution was allowed to cool to it under stirring while it was seeded with polymorph II to initiate crystallization. The stirring was continued for 12-24 h, the precipitated crystals were collected by filtration, washed with cold solvent(s) and dried to give 40 g of white crystals. HPLC assay: 99.9%.

F) 2-FL polymorph I (50 g) was dissolved in mixture of methanol (35 ml) and water (26 ml) and heated to 40° C. The solution was allowed to cool to rt under stirring while it was seeded with polymorph II to initiate crystallization. The stirring was continued for 12-24 h, the precipitated crystals were collected by filtration, washed with cold solvent(s) and dried to give 26 g of white crystals. HPLC assay: 98.2%.

G) Polymorph I (16.1 g) was suspended in ethyl acetate (80 ml) and water (8 ml), and stirred at 65-70° C. for 12 h. The solid was filtered and dried under vacuum to give 15.9 g of white crystals. HPLC assay: 98.6%.

X-Ray Powder Diffraction

XRPD investigations were conducted with a Philips PW1830/PW1050 instrument in transmission geometry, using CuKα radiation made monochromatic by means of a graphite monochromator. D-spacings were calculated from the 2Θ values, based on a wavelength of 1.54186 Å. As a general rule the 2Θ values have an error rate of ±0.2 Å.

DSC Analysis

The measurements were carried out on a SETARAM Labsys Evo TG-DSC thermoanalyzer, in flowing high purity (6.0) helium atmosphere (flow rate 20 ml/min) in the temperature range of 30-300° C. with a constant heating rate of 10 K/min, using standard 100 μl platinum crucible. Sample amounts varied between 5-10 mg.

An Example of Infant Formula

| Nutrient | per 100 kcal | per litre |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (70% FOS, 30% inulin) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.7 | 5 |
| 2-FL according to the present invention (mg) | 0.3 | 2.0 |
| B. lactis CNCM 1-3446 | $2 \cdot 10^7$ cfu/g of powder, live bacteria | |

An Example of Cake

| | |
| --- | --- |
| cake flour | 100 g |
| starch | 74 g |
| water | 14 ml |
| 2-FL according to the present invention | 30 g |
| baking powder | 2 teaspoons |
| salt | 2 teaspoons |
| egg | 1 |
| butter | 80 g |
| milk | 2 tablespoons |

Approx. 30 cookies can be produced from the ingredients above.

An Example of Powder Milk

| | |
| --- | --- |
| 2-FL according to the present invention | 20 g |
| skim milk | 5 kg |
| whey protein concentrate | 158 g |
| lactose | 924 g |
| le vitamin mixture | 75 g |
| minerals | 75 g |
| lipophilic vitamin | 578 g |

The ingredients are mixed, homogenized, sterilized and dried by means of routine methodologies to produce powder milk.

The invention claimed is:

1. Crystalline 2'-O-fucosyllactose polymorph II, characterized in that it displays X-ray powder diffraction reflections, based on a measurement using CuKα radiation, at 16.98±0.20, 13.65±0.20, 18.32±0.20, 21.70±0.20, 15.22±0.20, 20.63±0.20 and 11.94±0.20 2Θ angles.

2. The crystalline 2'-O-fucosyllactose polymorph II according to claim 1 which is substantially pure.

3. The crystalline 2'-O-fucosyllactose polymorph II according to claim 1 which is substantially free from organic solvent and/or water.

4. A method for producing crystalline 2'-O-fucosyllactose polymorph II according to claim 1, characterized in that syrupy 2-FL, solid 2-FL comprising amorphous 2-FL or 2-FL polymorph I, or a mixture of amorphous 2-FL and 2-FL polymorph I, is suspended in an ester type solvent.

5. 2'-O-Fucosyllactose polymorph I in polycrystalline or single crystal form, characterized in that it displays X-ray powder diffraction reflections, based on a measurement using CuKα radiation, at 21.34±0.20, 20.92±0.20, 18.37±0.20, 16.70±0.20, 9.91±0.20, 13.13±0.20, 7.87±0.20 and 8.90±0.20 2Θ angles.

6. The crystalline 2'-O-fucosyllactose polymorph I according to claim 5 in single crystal form, characterized in that it has monoclinic crystals, space group $P\,2_1$, with the following cell parameters: a=10.1781(11) Å, b=9.1990(9) Å, c=11.7332(13) Å, α=90.00°, β=107.871(3)°, γ=90.00°.

7. The crystalline 2'-O-fucosyllactose polymorph I according to claim 5, characterized in that it contains at most 30% of β-anomer.

8. The crystalline 2'-O-fucosyllactose polymorph I according to claim 5 which is substantially pure.

9. The crystalline 2'-O-fucosyllactose polymorph I according to claim 5 which is substantially free from organic solvent and/or water.

10. A method for producing crystalline 2'-O-fucosyllactose polymorph I according to claim 5 characterized in that the crystallization is carried out from a solvent system containing one or more $C_1$-$C_3$ alcohols and water, in the absence of seed crystals.

11. The method according to claim 10, wherein the $C_1$-$C_3$ alcohol is methanol and/or ethanol.

12. Pharmaceutical compositions comprising crystalline 2'-O-fucosyllactose polymorph II according to claim 1, and one or more pharmaceutically acceptable carriers.

13. Nutritional formulations comprising crystalline 2'-O-fucosyllactose polymorph II according to claim 1, as well as one or more constituents selected from edible micronutrients, vitamins and minerals.

14. A nutritional formulation according to claim 13, which is an infant formula, or a food supplement, or a digestive health functional food.

15. Pharmaceutical compositions comprising crystalline 2'-O-fucosyllactose polymorph I according to claim 5, and one or more pharmaceutically acceptable carriers.

16. Nutritional formulations comprising crystalline 2'-O-fucosyllactose polymorph I according to claim 5, as well as one or more constituents selected from edible micronutrients, vitamins and minerals.

17. A nutritional formulation according to claim 16, which is an infant formula, or a food supplement, or a digestive health functional food.

18. A method for producing crystalline 2'-O-fucosyllactose polymorph II according to claim 1, characterized in that the crystallization is carried out from a solvent system comprising one or more $C_1$-$C_6$ alcohols in the presence of seed crystals of crystalline 2'-O-fucosyllactose polymorph II.

19. The method according to claim 18, wherein the $C_1$-$C_6$ alcohol is methanol and/or ethanol.

20. The method according to claim 18, wherein the solvent system further contains water.

* * * * *